United States Patent
Ashtibaghaei et al.

(10) Patent No.: US 9,939,427 B2
(45) Date of Patent: Apr. 10, 2018

(54) METHOD FOR EVALUATING THE SCENT PERFORMANCE OF PERFUMES OR PERFUME MIXTURES

(71) Applicant: Symrise AG, Holzminden (DE)

(72) Inventors: Kaveh Ashtibaghaei, Bochum (DE); Günter Gisselmann, Witten (DE); Hanns Hatt, Bochum (DE); Johannes Panten, Höxter (DE)

(73) Assignee: Symrise AG, Holeminden (DE)

( * ) Notice: Subject to any disclaimer, the term of this patent is extended or adjusted under 35 U.S.C. 154(b) by 0 days.

(21) Appl. No.: 14/568,976

(22) Filed: Dec. 12, 2014

(65) Prior Publication Data
US 2015/0260707 A1 Sep. 17, 2015

(30) Foreign Application Priority Data
Dec. 15, 2013 (EP) .................... 13 197 310

(51) Int. Cl.
*G01N 33/50* (2006.01)
*C12Q 1/66* (2006.01)
*G01N 33/566* (2006.01)

(52) U.S. Cl.
CPC .......... *G01N 33/5041* (2013.01); *C12Q 1/66* (2013.01); *G01N 33/566* (2013.01); *G01N 2500/04* (2013.01)

(58) Field of Classification Search
None
See application file for complete search history.

(56) References Cited

FOREIGN PATENT DOCUMENTS

| JP | 11-128693 A | 5/1999 |
|---|---|---|
| WO | 03/091388 A2 | 11/2003 |

OTHER PUBLICATIONS

Keller et al., Genetic variation in a human odorant receptor alters odour perception, Sep. 27, 2007, Nature 449:468-472.*
Zhuang et al., Evaluating cell-surface expression and measuring activation of mammalian odorant receptors in heterologous cells, 2008, Nat Protoc. 3(9):1402-1413.*
Schmiedeberg et al., Structural determinants of odorant recognition by the human olfactory receptors OR1A1 and OR1A2, 2007, Journal of Structural Biology 159:400-412.*
Koyano et al., Common null variant, Arg192Stop, in a G-protein coupled receptor, olfactory receptor 1B1, associated with decreased serum cholinesterase activity, Jul. 1, 2008, Hepatology Research 38(7):696-703.*
Krautwurst, D., Human Olfactory Receptor Families and Their Odorants, 2008, Chemistry & Biodiversity 5:842-852.*
Baghei, Kaveh, "Deorphanization of Human Olfactory Receptors by Luciferase and Ca-Imaging Methods," Methods in Molecular Biology 2013, vol. 1003, Jun. 19, 2013, pp. 229-238.
Baghei et al, "Olfactory receptors coded by segregating pseudo genes and odorants with know specific anosmia," 33rd Annual Meeting of the Association for Chemoreception, Apr. 1, 2011, Abstract.
Touhara et al, "Deorphanizing vertebrate olfactory receptors: Recent advances in odorant-response assays," Neurochemistry International, vol. 51, Nos. 2-4, Aug. 6, 2007, pp. 132-139.

* cited by examiner

*Primary Examiner* — John D Ulm
(74) *Attorney, Agent, or Firm* — Dilworth & Barrese, LLP

(57) ABSTRACT

Proposed is a method for evaluating the scent performance of perfumes or perfume mixtures, wherein at least one odorants is brought into contact with an olfactory receptor selected from the group consisting of OR1B1, OR2L8, OR4X2, OR4C16, OR5L1, OR8B4, OR8D2, OR10A6, OR10C1, OR12D2, OR524, OR4E2, OR4P4, OR4K2, OR4C3, OR5I1, OR10Q1 and measuring the response of the receptor.

7 Claims, 17 Drawing Sheets
(4 of 17 Drawing Sheet(s) Filed in Color)

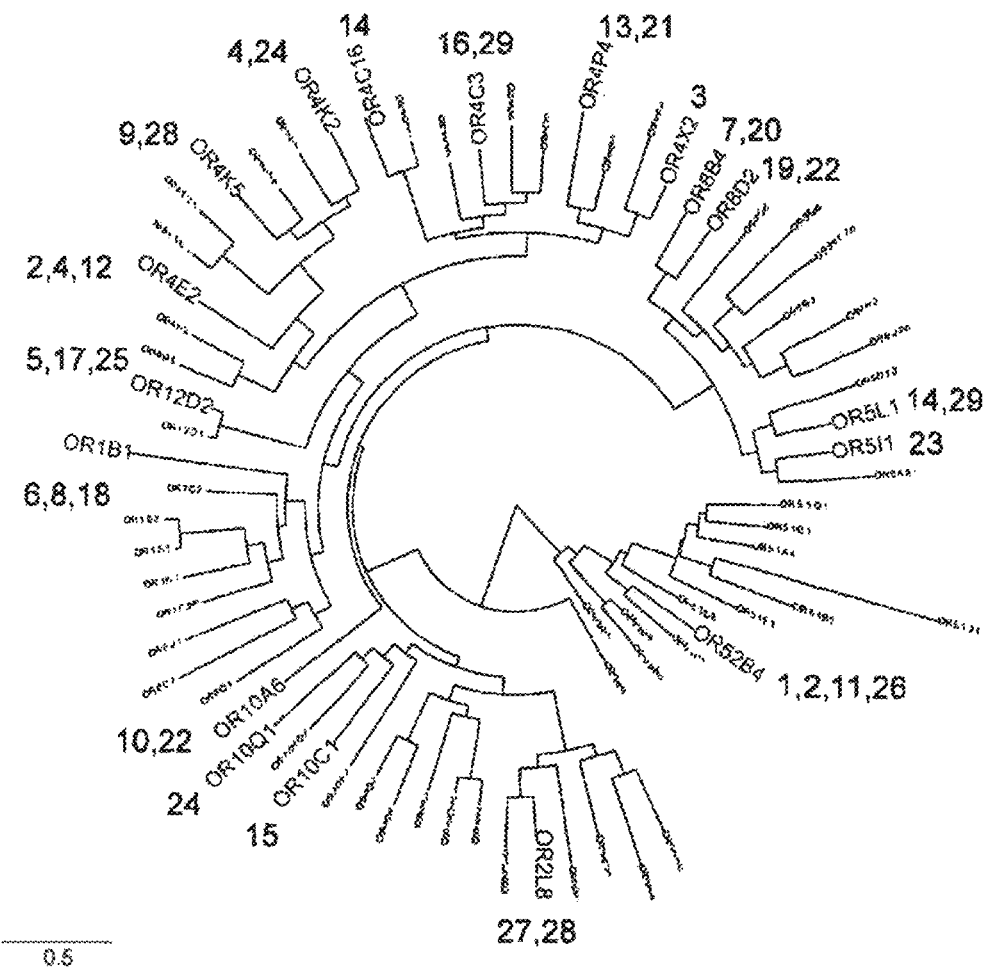

| | | | | | |
|---|---|---|---|---|---|
| 1 | 1-Octan-3-one | 11 | Geosmin | 21 | n-Hexanoic acid |
| 2 | 2,4,6-Trichloroanisole | 12 | Geraniol | 22 | n-Hexanol |
| 3 | 2-Aminoacetophenone | 13 | Globalide | 23 | n-Octanal |
| 4 | 3-Phenyl propyl aldehyde | 14 | γ-Nonalactone | 24 | Pentadecalactone |
| 5 | Acetic acid | 15 | Hedione | 25 | Propionic acid |
| 6 | Androstenone | 16 | Isocaproic acid | 26 | Sandranol |
| 7 | Anisic aldehyde | 17 | Isovaleric acid | 27 | Timberol |
| 8 | Calone | 18 | Maltol | 28 | Ysamber K |
| 9 | Cedramber | 19 | Muguet alcohol | 29 | β-Damascone |
| 10 | Cinamyl alcohol | 20 | n-Hexanal | | |

Fig. 9B

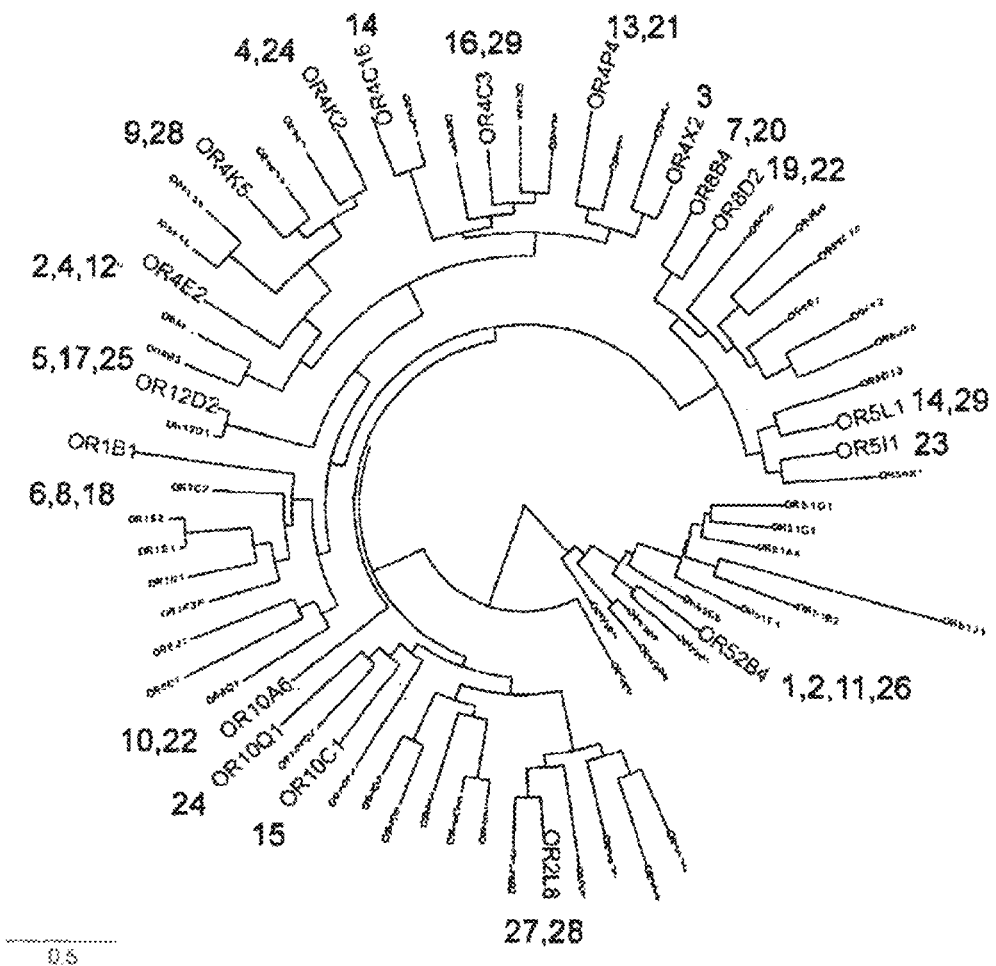

| | | | | | |
|---|---|---|---|---|---|
| 1 | 1-Octan-3-one | 11 | Geosmin | 21 | n-Hexanoic acid |
| 2 | 2,4,6-Trichloroanisole | 12 | Geraniol | 22 | n-Hexanol |
| 3 | 2-Aminoacetophenone | 13 | Globalide | 23 | n-Octanal |
| 4 | 3-Phenyl propyl aldehyde | 14 | γ-Nonalactone | 24 | Pentadecalactone |
| 5 | Acetic acid | 15 | Hedione | 25 | Propionic acid |
| 6 | Androstenone | 16 | Isocaproic acid | 26 | Sandranol |
| 7 | Anisic aldehyde | 17 | Isovaleric acid | 27 | Timberol |
| 8 | Calone | 18 | Maltol | 28 | Ysamber K |
| 9 | Cedramber | 19 | Muguet alcohol | 29 | β-Damascone |
| 10 | Cinamyl alcohol | 20 | n-Hexanal | | |

Fig. 9C

Responsiveness of OR1B1-574 to androstenone (left) and testosterone (right) in comparison to OR1B1 WT as examined by Ca-imaging measurements on receptors heterologous expressed in HEK293 cells.

No significantly different responses of OR1B1-688 and OR1B1-789 to androstenone (left) and testosterone (right) in comparison to OR1B1 WT as examined by Ca-imaging measurements on receptors heterologous expressed in HEK293 cells.

Similar responses of OR10Q1-614 to pentadecanolide in comparison with OR10Q1 WT as examined by Ca-imaging measurements on mutated and WT receptor heterologous expressed in HEK293 cells.

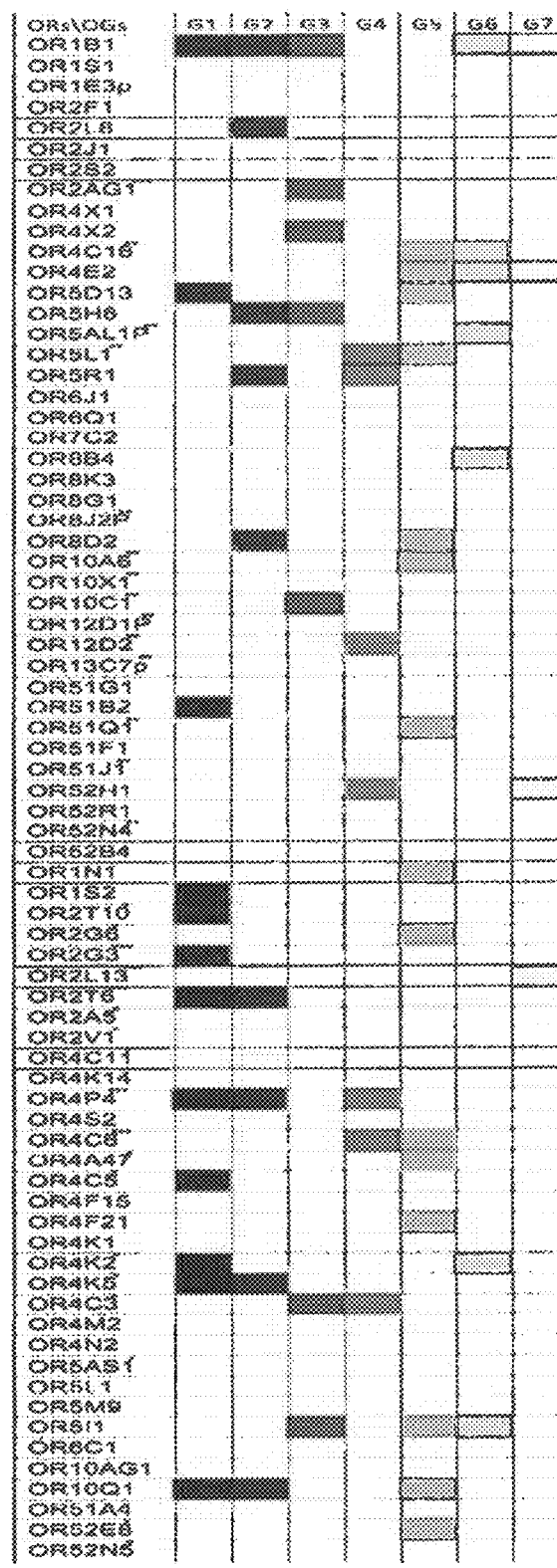
Fig. 14 ORs respond to odorant groups (OGs)

METHOD FOR EVALUATING THE SCENT PERFORMANCE OF PERFUMES OR PERFUME MIXTURES

FIELD OF INVENTION

The present invention belongs to the area of aromas and scents and refers to a new method for evaluating and identifying the scent performance of perfumes or perfumes mixtures by exposing them to specific olfactory receptors.

STATE OF THE ART

The human olfactory system has the remarkable capacity to recognize and discriminate a large number of different chemical components and odor molecules. As a chemical sensor, the olfactory system is effective on social and sexual behavior and quality of life because the odorant can evoke memories and emotions or influence our mood.

Odorant perception starts with the chemical interaction between an odorant molecule and an olfactory receptor expressed in an olfactory sensory neuron (OSN). These neurons are located in the olfactory epithelium (OE), which is covered with a mucous layer which supplies lipid/protein-rich secretions for the OE surface. Most parts of the human nasal cavity consist of ciliated columnar respiratory epithelial tissue. The upper section of the nasal cavity, lining the cribriform plate, consists of OSNs. OSNs are bipolar cells with a single unbranched dendrite with axons penetrating through the cribriform plate to the olfactory bulb of the brain. Axons of mitral cell then leave the olfactory bulb (OB) to higher brain structures including the piriform cortex, hippocampus and amygdale. About 10-25 cilia, each ~5 μm long, extend from the knob of each OSN. Each OSN expresses just one type of olfactory receptor (OR) protein which is the first level for the primary events of chemo-sensory transduction. Each OSN expresses just one type of olfactory receptor (OR) protein which is the first level for the primary events of chemo-sensory transduction.

The olfactory system can differentiate among thousands of chemical components by olfactory receptors as one of the key components of the molecular decoding device of the nose. ORs, such as visual opsins, bitter and sweet taste receptors (TAS2R1 and TAS1R1) and vomeronasal receptors (V1Rs, V2Rs and V3Rs), are encoded by a large gene super family, belonging to G-protein-coupled receptors (GPCRs). They are identified by several characteristic sequence motifs and constitute the largest gene family in the mammalian genome. GPCRs have a common structural feature with seven α-helical transmembrane (TM) regions. They can be classified into six groups by sequence similarities and OR genes belong to a rhodopsin-like the GPCR superfamily, which is the largest of them.

This gene super family is organized into 18 gene families and 300 subfamilies and localized in multiple clusters of varying sizes distributed on all autosomes except chromosomes 20 and Y. The two largest OR gene clusters are located on chromosomes 11 with 38 functional genes on 11q and 44 functional genes on 11p. Based on the percentage of similar amino acid sequences, OR genes can be grouped into a particular family and furthermore into a subfamily. ORs with >40% protein sequence identity are considered to be within the same family, and if they share >60%, they belong to the same subfamily. In accordance with this concept, OR genes are classified by the HUGO Gene Nomenclature Committee (HGNC).

ORs are ~310 amino acids long on average. The sequence of OR genes revealed remarkable diversity in transmembrane (TM) helices 3 to 6 between paralogs, likely accounting for the high diversity in ligand specificity. There are several motifs that are characteristics of ORs. One such motif is 'MAYDRYVAIC' (SEQ ID NO: 1), located at the junction of TM3 and the intracellular loop between TM3 and TM4. Within this motif, the stretch of three amino acids, 'DRY' (aspartic acid-arginine-tyrosine), is highly conserved among rhodopsin-like GPCRs. The DRY motif is possibly important for G-protein coupling. It is supposed that in the OR repertoire, contact positions show pronounced variability between paralogs. Later studies have tried to consider odorant binding residues in olfactory receptors based on sequence analysis. Some approaches together predicted 22 putative contact residues, located on TMs 3 to 7 in their models. In a recent study, it is provided by combining dynamic homology modeling with site-directed mutagenesis and functional analysis, a molecular model of the ligand-binding site to predict receptor function based on computational information.

Segregating Pseudogenes (SPG)

Human OR contains a high number of pseudogenes, whereby more than 50% of the loci are nonfunctional due to frame-disrupting mutations.

A fraction of the human olfactory receptors could be segregated between an intact and pseudogene form of olfactory receptor. In other words, some olfactory receptor genes display both functional and non-functional allels, which are called segregating pseudogenes. They are explained as genes that segregate in populations between intact genes and pseudogenes due to a disruptive disruption single nucleotide polymorphism (SNP). This divider mutation can introduce a stop codon, or alter a highly conserved amino acid that is important for proper function of the protein.

The first studies in 2003 conducted by Gilad and Lanet [Mol. Biol. Evol 20(3), p. 307-314 (2003)] revealed 12 SPGs in humans. Their results show frequencies of intact alleles in Pygmies (an African population) more than in Caucasians. In the same year Menashe et al. [Nat. Genet. 34(2), p. 143-144 (2003)] extrapolated the number of segregating olfactory receptor pseudogenes in the entire human genome to at least 60. They found that African Americans have more functional ORs than non-African participants. In 2012 the number of SPGs jumped to 244 when Lancet's group reported an unusually high genetic diversity in the OR gene repertoire among individuals and suggested that individual humans have highly personalised "barcodes" of functional olfactory receptors. In Olender's study every human individual is personalised by a different combination of such SPGs. One of the most accepted hypotheses is that allelic variants of OR genes may produce different functional characteristics that can lead to the generation of different odorant sensitivity phenotypes in the human population. An association study between SPGs and odorant sensitivity showed a high association between forms of the OR11H7P gene and sensitivity to isovaleric acid, who are heterozygous or homozygous for the intact allele of OR11H7P were more likely to be hyperosmic to isovaleric acid than individuals who are homozygous for the disrupted allele. It could be mentioned that potential ligands for deorphanized ORs can generally be used in association studies to determine detailed relationships between individual olfactory receptor disruption and odorant perception variability.

Copy Number Variation (CNV)

CNVs caused by genomic rearrangements can generate phenotypes by different molecular mechanisms such as:

gene dosage, gene interruption, gene fusion and position effects or unmasking of recessive alleles. Some of the association between CNVs and phenotype variation are involved in human diseases. The best-known example is Down syndrome caused by trisomy of human chromosome 21; another would be thalasemia due to alpha globin gene rearrangements.

CNVs have been defined as "a segment of DNA that is 1 kb or larger and is present at a variable copy number in comparison with a reference genome". This explanation was modified, based on a functional definition, and it was suggested that we should choose an average exon size (~100 bp) as a parameter for defining CNV. Copy number variations are a source of genetic diversity in humans. When the breakpoint of a deletion, insertion or duplication is located within a functional gene, it may interrupt the gene and cause a loss of function by inactivating a gene as described by red-green opsin genes and color blindness.

In genome-wide studies, CNVs for a larger number of OR genes or gene clusters were detected. In a previous study, individual CNVs of OR genes were systematically investigated. In a panel of approximately 50 human individuals, copy-number variations of 18 ORs were confirmed. No individual had the full number of functional OR genes expected from the reference genome data and virtually every individual had a unique combination of functional losses and gains among the ORs, thus demonstrating that CNVs generate individual patterns of OR genes. In a study conducted by Waszak [PLos. Comput. Biol. 6(11) pp e1000988 (2010)] it is reported that deleterious variants including CNVs and SNPs affect 15% and 20% of the human OR gene repertoire, respectively. They revealed that OR loci display an extensive range of locus copy-numbers across individuals, with zero to nine copies in OR loci. A recent study by Olender in 2012 showed an increased number of CNVs to 66% of intact OR loci. They reported that of the 851 human genomic OR loci, 438 have a frame-disrupting pseudogene apparently fixed in the entire population. Of the 413 remaining loci, 271 (66%) have at least one allele lacking an intact open reading frame, including frame disruptions and deletion CNV alleles.

Table 3 illustrates olfactory receptots (ORs) respond to odorant groups (OGs).

The presence of these copy number variations can induce genomic structural variation in specific gene families as well as at a genome-wide scale by gene duplication or exone shuffling. So, CNVs could be one of the reasons for the significant variations in olfactory capabilities among human individuals. However, the relation of CNV to odor perception remains to be evaluated.

Olfactory Signal Transduction Pathways

The canonical pathway of signal transduction in OSNs of mammals is composed of the OR as one variable component and four constant elements: the Gaolf-containing heterotrimeric G-protein; adenylyl cyclase, which produces the second messenger cAMP; a cyclic nucleotide-gated cation channel and a Ca-activated chloride channel. Olfactory sensory neurons express a G-protein with a specific subunit named Gaolf. With binding of an agonist to the OR, Gaolf activates an olfaction-specific adenylate cyclase that leads to activation of cAMP. Following this cascade, cyclic nucleotide-gated channels (CNG) will be opened by increasing of cAMP level. Inactive OSNs normally maintain a resting potential across their plasma membrane of about −65 mV (inside with respect to outside). The opening of the channel is depolarised of neuron membranes by influx of sodium (Na+) and calcium (Ca2+) ions. The Ca2+-influx also causes the opening of a Ca2+-dependent-Cl−-channel, which enhances the depolarising of the cell membrane and generates action potentials. along the sensory axons, leading to signal transmissions to the olfactory bulbs.

The adenylyl cyclase (AC)/cAMP pathway is essential for olfactory responses in vertebrates. However, odorants activate more than one transduction cascade; IP3 has also been shown to be an efficient second messenger. Fundamental to an emerging concept of multiple olfactory signalling pathways was the observation that some odors did not elicit a rise in cAMP in biochemical assays. Instead, such 'non-cAMP odors' appeared to induce phospho-inositide signalling in olfactory cells. Also, a possible involvement of inositol 1,4,5-trisphosphate (InsP3) in olfaction was reported for a variety of species. In 2005 it was explained that phosphatidylinositide-related signaling proteins, including phospholipase C beta-2 (PLC b2), InsP3-receptor type III (InsP3R-III) and classical transient receptor potential channel 6 (TRPC6), are colocalised in a distinct population of microvillus cells in the olfactory epithelium of mammals. They showed the presence of a novel class of secondary chemosensory cells in the olfactory epithelium of mammals that utilize phosphatidyl-inositides as second messengers in signal transduction.

However, it was reported that in vivo different chemical components could activate the cAMP or IP3 pathways or both of them. However, the correlation with the in vitro tests performed in heterologous cell system is still not clear today.

Functional Expression of Recombinant Olfactory Receptors in Heterologous Systems Understanding of OR function has improved slowly due to a lack of suitable heterologous systems for expression and assays on odorant responses. Expression of GPCRs is a complex process that includes protein folding, posttranslational modifications, and transport through cellular compartments including the endoplasmic reticulum and Golgi apparatus. One main reason for the inadequate functional expression of ORs is that the receptors do not reach the cell membrane of heterologous cells. They remain in the endoplasmic reticulum as a result of inefficient folding and poor coupling to the export machinery, combined with aggregation and degradation through both proteosomal and autophagic pathways.

Studies in the last decade have developed the expression of ORs in heterologous systems. Several attempts have been made to achieve functional expression of ORs on the cell surface in heterologous systems. In some cases, fusion of the 20 N-terminal amino acids of the rhodopsin or serotonin receptor to the N-terminal region of ORs resulted in a limited expression of functional ORs in the plasma membrane and induced a successful odorant-response in a heterologous system such as HEK293 cells. It has been shown that glycosylation of the N-terminus of ORs is required for proper translocation to the plasma membrane. Tagged ORs could be co-transfected in heterologous cells with the Gα subunits. The dissociated Gα and Gβγ subunits activate a widespread variety of effectors, including adenylyl cyclases, phospholipases and plasma membrane channels. The primary effectors of Gs and Gq coupled signalling pathways are adenylyl cyclase and phospholipase C, respectively (Chen et al. 1995). The Gs subunit usually involves the activation of adenylyl cyclase and measurement of cAMP concentration by radioimmunoassay, while activation of the Gq subunit is commonly assayed by measurement of the production of inositol triphosphate or diacylglycerol from phosphatidiylinositol 4,5-bisphosphate or by changes in intracellular calcium.

Other important cofactors that help to transport ORs to the cell membrane are receptor transporting proteins (RTPs) 1 and 2 and receptor expression enhancing protein (REEP) 1. One transmembrane protein, RTP1, which has been referred to as an OR chaperone, appears to enhance cell surface expression of ORs, and many ORs have been deorphanized by coexpressing them with RTP1.

In association with ORs, some G-protein activating enhancers have been co-expressed to improve the olfactory signal transduction. Guanine nucleotide exchange factors (GEF) could increase activation of G-proteins. Ric-8B, as a known GEF expressed in olfactory sensory neurons, is able to interact with Gaolf. GEFs catalyse the exchange of GDP for GTP to generate an activated form of Gα, which is then able to activate a variety of effectors. Ric-8A and Ric-8B are GEFs in the mammalian olfactory system. While Ric8A can interact with the Gαq, Gαi and Gαo classes of Gα subunits, Ric-8B interacts with the Gαs class. It has been shown that Ric-8 (A and B) promotes efficient functional expression of ORs in heterologous systems. It has also been shown that a myristoylation sequence—conjugated mutant of Ric-8A (Myr-Ric-8A) could be used as a signal amplifier and Myr-Ric-8A greatly enhances Ga15-mediated Ca2+ responses of ORs in HEK293 cells. Myr-Ric-8A as a cofactor that enhances OR-mediated Ca2+ signaling in HEK293 cells should be helpful in functional expression of ORs in heterologous cells by using Ca-imaging.

In addition, the expression of ORs could be supported by the presence of the Hsc70 protein. Hsc70t, which belongs to the Hsp70 family of genes, is expressed exclusively after meiosis in mouse spermatogenesis. In addition, it might be involved in the folding or trafficking of olfactory receptors. Co-transfected HEK293 cells with Hsc70t and odorant receptors (ORs) from mice and humans show a significantly enhanced OR expression. Hsc70t expression also changes the quantity of cells functionally expressing olfactory receptors at the cell surface so the number of cells responding to odorants in Ca-imaging experiments will be increased significantly.

Thus, introduction of the factors required for OR expression indicate that cell surface expression of ORs as a critical level for OR assays can be significantly improved by co-expression with auxiliary proteins that associate in OR trafficking to the cell surface, and it is expected that these proteins solve the problems of cell surface expression of ORs.

Odorant Perception

An odorant is a substance capable of eliciting an olfactory response whereas odor is the sensation resulting from stimulation of the olfactory organs. Odors play an important part in our everyday life, from appetite stimulation to serving as warning signals. The general criterions for an odorant are: it should be volatile, hydrophobic and have a molecular weight less than approximately 300 Daltons. In explanation of odor perception, odor threshold should be noted. This term used to determine the lowest concentration of particular odorant to which animals (humans) responded 50 per cent of the time to repeated presentations of an odorant. Thresholds for odorants vary greatly between individual persons and it is base of classification of odorants in terms of the intensity to weak and strong according to efficacy and affinity.

The perception of odorants always happens as a complex mixture of different odor molecules. For example, the smell of a rose constitutes 260 chemical components. In some sensory modalities, the magnitude of mixed stimuli is perceived as the sum of the magnitudes of the individual stimuli; this property is known as additivity. The estimated intensity of the smell of the mixture of two odorants is frequently perceived as being non-additive. This phenomenon is called "counteracting". There are three types of counteracting: "partial addition, in which the mixture smells more intense than the stronger component; compromise, in which the smell intensity of the mixture is in between the intensities of the components; and compensation, in which the mixture smells less intense than the weaker component".

Many theories have in the past been proposed to describe the mechanism of smelling odorants, but advances in biological understanding, not least of which being the discovery of odorant receptors, have gradually ruled them out. One of these is physical theory that proposes the shape of the odorant molecule determines which olfactory receptor cells will be reacted. This theory is based on fragments of molecular shape and molecular vibrations.

Chemical Structure Basis of Odorant

To understand the association between odorants and receptors, it is necessary to know which properties of odorant or odor descriptors are critical for interaction with olfactory receptors. It has been proposed that the majority of olfactory receptors respond to multiple odors. Although different in many respects, they should share certain molecular properties such as functional groups. These properties mostly gravitated toward the chemical structure of odorants, carbon atom number (CAN), functional group type and position, which are parts of odor descriptors that have been determined in recent olfaction research. It has been shown by different studies that olfactory sensory neurons respond to molecules with similar CAN, pending these molecules share the same functional group. ORs that respond to odorants with 5 carbons have similar responsiveness to odorants with 4 or 6 carbons but are less likely to respond to odorants with 7 or more carbons. This means odorants that have similar CAN and functional groups elicit similar response patterns. With regard to functional groups, the testing of one rat olfactory receptor (17) with 90 odorants of different chemical structures suggested the carbonyl aldehyde group is critical for the activity of odorant at the 17 receptor. Also, a similar experiment was done with *Drosophila melanogaster* olfactory sensory neurons and 110 odorants of diverse functional groups.

It should be noted that not all descriptions of odorants are in accordance with chemical structure and, in some examples, conception of odors is not explicable by ant structure. Two wellknown instances are musks and ambers.

Musk is one of the most famous odorants. Because of its universal inclusion in fragrance and due to expense and legislation it has been synthetic for a long time. The molecules that indicate musk odor properties are diverse in structure. The other group of odorants is amber which was originally produced by whales. Ambers make an interesting combination of closely related smells with widely different structures: timberol, karanal and cedramber are close enough that a perfumer will occasionally confuse them with each other, as for example the following molecules from amber group, with widely different structure but similar odorant perception.

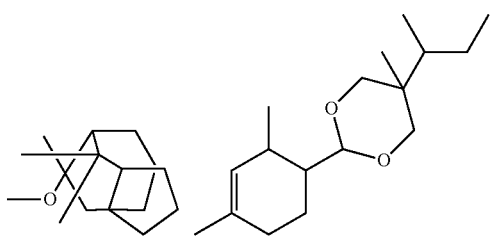

Cedramber        Karanal

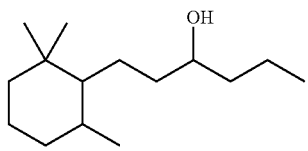

Timberol

In other part there are enantiomers which make completely different smell, one of the examples is R and S carvone that smell of R carvone is minty and S carvone is caraway.

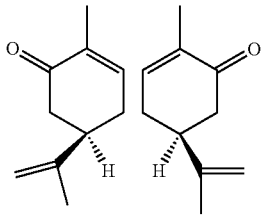

Also the following isomers have effect on odorant intensity:

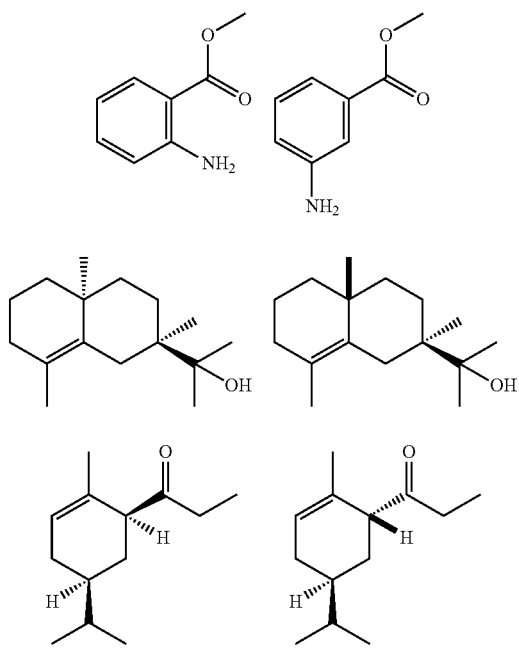

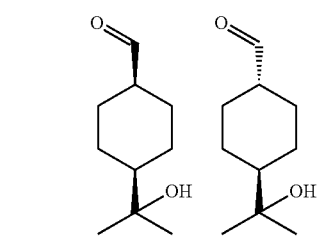

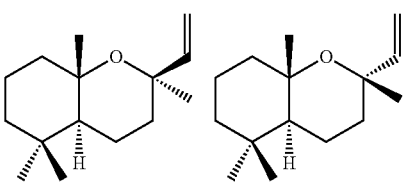

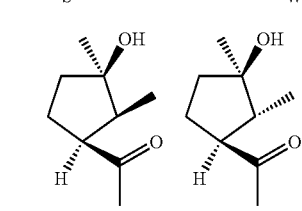

Shown are the following molecules: 1-methylanthranilate, 2-eudesmol, 3-neron, 4-p-menthane derivatives, 5-caparrapi oxide, 6-iridanes. In every case, the strong isomer is in left and weak isomer is right one.

In agreement with responses of olfactory system, Wetzel et al. reported that a receptor only responded to helional at very low concentrations but not to piperonal with closely related chemical structure [J. Neurosci. 19(17) p. 7426-7433 (1999)].

Olfactory Dysfunction

Odorant perception is most variable sense among different individuals. This variation is reflected in olfactory dysfunctions and normal physiological variation such as specific anosmia. Distribution of olfactory dysfunction in human population is a matter of debate. However, most studies reported frequencies of 1% to 3% of chemosensory disorders. Different reasons are reported as factors in occurrence of smell dysfunction. One of the main reasons of olfactory dysfunction is a process that directly affects and impairs either the olfactory epithelium or olfactory pathways. Olfactory disorders can be categorized in different groups:

1) anosmia: missing olfactory sensations and it is complete loss of smell function,
2) partial anosmia: ability to perceive some, but not all of odorants,
3) hyposmia or microsmia: a general decreased sensitivity to odorants,
4) hyperosmia: unusual acute smell function (increasing sense of smell), as an increased sensitivity to all odors,
5) olfactory agnosia: inability to recognize an odor sensation,
6) dysosmia (cacosmia or parosmia): When a normal pleasant odor is perceived as a unpleasant odorant,
7) phantosmia: dysosmic sensation perceived in the absence of an odor stimulus and
8) specific anosmia: The inability to smell one of a few odorants in the presence of an otherwise normal sense of smell.

Specific Anosmia

A major theoretical of specific anosmia was made by Marcel Guillot in his paper entitled 'Anosmies partielles et odeurs fondamentales' in 1948. Amoore used new term instead of partial as 'specific anosmia', and explained it "the condition which a person of otherwise normal olfactory acuity cannot perceive a particular compound, at a concentration such that its odor is obvious to most other people". In complimentary description about specific anosmia is explained, most often a person has a 10-100 fold diminished sensitivity to a given odorant, out of this range it could be refer to exact term as specific hyposmia. The first anosmic defects were pointed out for isovaleric acid, 1-pyrroline, trimethylamine, isobutyraldehyde, 5α-androst-16-en-3one and pentadecalactone by Amoore.

A known example for anosmia is androstenone (5α-androst-16-en-3-one), with 30% rates of specific anosmia, some individuals with normal sense of smell are unable to detect the odor of androstenone (5α-androst-16-en-3-one) at the concentrations tested, and those who are able to perceive it describe the odor in different ways as: sweaty, urinous, musky, sweet, or even perfume-like.

Diversity of quality descriptors for a one given odorant is named specific allosmia, and the term specific anosmia describes the inability of some people to smell an odorant. Therefore, the perception of androstenone is an example of both a specific allosmia and anosmia.

Geneticists have been interested in the ability to smell androstenone because the expectation is that individual differences can be explained by a deleterious allele in a particular narrowly tuned olfactory receptor and it is shown by various studies that anosmia to androstenone is highly concordant in monozygotic twins and ability to detect androstenone is a heritable trait. This hypothesis has proved to be partially true, A novel approach showed that a combination of two non-synonymous SNPs (R88W and T133M) in the human OR gene OR7D4 accounts for 19-39% of the variation in sensitivity and quality perception of androstenone. The study found that subjects with at least one copy of the WM haplotype are less sensitive to androstenone than those that do not carry a WM allele. These results provided for the first time the link between genetic variation in OR and odor perception.

Associations between olfactory receptor alleles and perception are observed not only for androstenone but also for isovaleric acid, asparagus metabolites, and cis-3-hexen-1-ol. Isovaleric acid is one of the first evidence for specific anosmia in humans (Russell et al. 1993). A genetic study showed an association signal between isovaleric acid sensitivity and the genotype of a segregating OR pseudogene OR11H7P on human chromosome 14. Also in early studies heritability has been shown for the sensitivity to pentadecalactone as a musky odorant.

Regarding to subject of relation between specific anosmia and genetic variation, it is supposed that if an odorant is recognized by one particular OR, mutations in that OR could be lead to specific anosmia for the odorant, but if an odorant is recognized by more than one OR, specific anosmia would not occur unless all of the relevant ORs were mutated. However, it should be noticed that these genetic associations could not explain specific anosmia entirely. Olfactory sensitivity may be influenced by gender or some environmental and behavioral factors have also been suggested to affect olfactory proceeds.

Summing up the state of the art it is well known that interaction of odorants with olfactory receptors is the initial step in odorant detection. Olfactory receptors are the largest group of G protein-coupled receptors. These receptors are presenting worldwide with genetic variations which are hypothesized to influence on their functions. However, still just a small number of agonists were identified out of thousands of odorants. Due to this compelling complexity, the identification of receptor-ligand pairs was and is still in its infancy and just a handful of human cognate receptor-ligand pairs are known so far. Elucidation of general properties of the olfactory system, such as determination of the general similarity between some odorants and ORs, requires investigation of a large number of diverse ORs with chemically diverse odorants in a consistent assay. Availability of the complete sequence of human genome and quantitative data for millions of SNP gained from the 1000 genomes project and other sources provides enormous opportunities to relate olfactory phenotype to the underlying genotype of odorant receptor genes.

Therefore the problem underlying the present invention has been to relate specific anosmias (encountered in various populations) with the underlying gene mutations and to develop a method for evaluating the scent performance of perfumes or perfume mixtures, in particular for those products which are known to be recognized by a limited number of individuals only.

Another object of the present invention has been to identify deorphanized receptors to address several distinct questions such as quantification of odorant similarity, quantification of receptor similarity and receptor code of an odorant is composed of ORs that are "narrowly tuned" to a few odorants or "broadly tuned" to recognize many odorants.

DESCRIPTION OF THE INVENTION

Object of the present invention is a method for evaluating the scent performance of perfumes or perfume mixtures, wherein at least one odorant is brought into contact with an olfactory receptor selected from the group consisting of OR1B1, OR2L8, OR4X2, OR4C16, OR5L1, OR8B4, OR8D2, OR10A6, OR10C1, OR12D2, OR524, OR4E2, OR4P4, OR4K2, OR4C3, OR5I1, OR10Q1 and measuring the response of the receptor.

Surprisingly, it has been observed that the cited ORs have the capability to respond to one or more odorants, in particular to those odorants which are subject to anosmia, that means they are known to be recognized only by a limited number of individuals only.

BRIEF DESCRIPTION OF THE DRAWINGS

The patent or application file contains at least one drawing executed the color. Copies of this patent or patent application publication with color drawings will be provided by the Office upon request and payment of the necessary fee.

The present invention will be described in greater detail with reference to the accompanying drawings in which FIG. 1 schematically illustrates cloning of ORs;

FIGS. 9A, 9B and 9C each illustrate a phylogenic tree of 74 olfactory receptors which are known as SPGs or CNVs;

FIG. 14 illustates olfactory receptors (ORs) respond to odorant groups (OGs)

DESCRIPTION OF THE PREFERRED EMBODIMENTS

Figure 1:
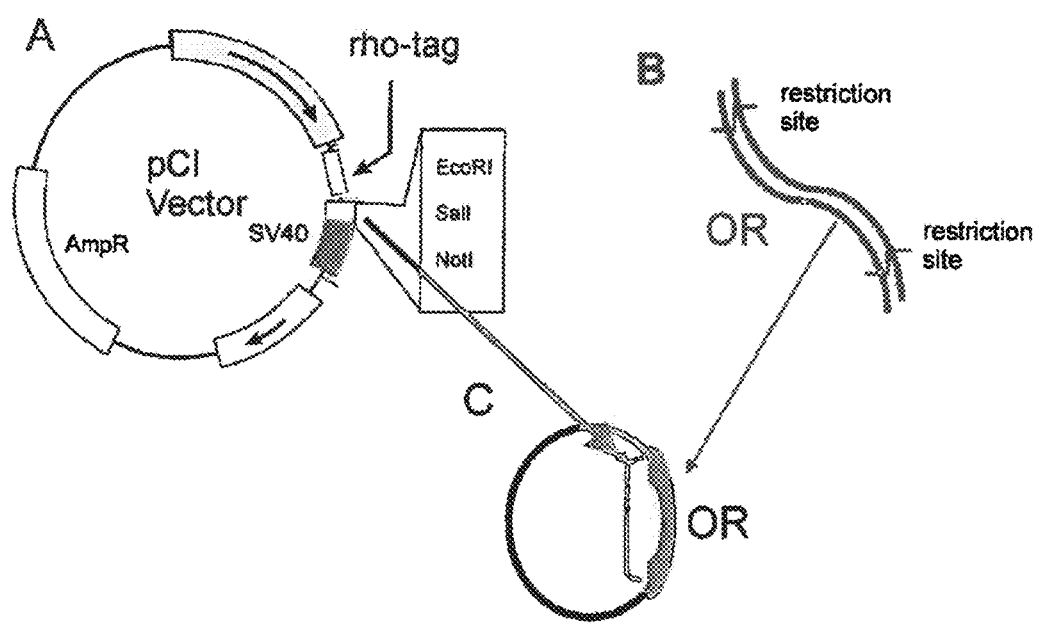

Large Scale Investigation of ORs Including SPGs and CNVs

It is known that the OR genes repertory is one of the most genetically diverse regions in the human genome and it contains thousands of deletions or duplications of DNA segments greater than 1 Kb in size (CNV), which are present in some individuals but not in others, and also a large number of single nucleotide polymorphisms (SNPs), some of which lead to the inactivation of OR genes (i.e. segregating pseudogenes).

It is known from the state of the art that the genetic basis of human olfactory variations by focusing on a subset of olfactory receptor genes with widespread mutations that disrupt their coding region and destroy their function. Because these genes coexist with their intact counterparts in the human population (and are thus called segregating pseudogenes, or SPGs), it seems they are promising candidates for explaining human variance in odor detection and to find a relation between genetic variation and anosmia as a kind of phenotype variation in human odorant perception. In this study, we focused on a large-scale analysis of genetically polymorphic odorant receptors.

As described in several studies, there are links between genetic variation in OR and odor perception. Specific anosmia is thought to arise from mutations in olfactory receptor genes; however, no mutation in humans has as yet been linked to specific anosmia. It is suspected that variations in the genes that encode olfactory receptors, which function on the front line of odor recognition, may explain the vast differences seen in humans' ability to detect odors. In several examples it has been demonstrated that variation in OR genes by SNPs is a major reason for this kind of difference. Also, it is suggested, SPGs have donor potential for variation in human odor perception. With regard to these properties, 40 orphan SPGs and 34 of the most abundant CNVs were chosen and tested with odorants related to anosmia. By a calcium imaging technique we identified 32 agonists for 18 human ORs including SPGs and CNVs. The results show that, out of 40 SPGs, 12 ORs (30%) and, out of 34 CNVs, 6 ORs (18%) were activated by odorants related to specific anosmia.

In part of the study, OR1B1, OR2L8, OR4X2, OR8D2 and OR8B4 were deorphanized as SPGs with minor allel frequency (MAF of SNPs occurred as a point mutation in a highly conserved amino acid) of 33%, 22%, 16%, 50% and 26% respectively for odorants including 3-hydroxy-2-methyl-4pyran, Calone, androstenone, testosterone, Yasamber, Timbrol, 2-aminoacetophenone, Anisic aldehyde, aldehyde C6, alcohol C6 and Muguet alcohol. Among all odorants, androstenone is one of the best characterised chemical components. Androstenone (5a-androst-16-en-3-one) is reported as an odorous steroid derived from testosterone, and is variously perceived by different individuals as offensive ("sweaty, urinous"), pleasant ("sweet, floral") or odorless. Depending on the study, between 11% and 75% of the population is unable to detect the odor of androstenone. This variation in the ability to perceive androstenone might suggest that androstenone perception is in part determined genetically.

As some family studies have shown, androstenone thresholds are more similar among identical twins compared with fraternal twins (0.95 and 0.22, respectively) and concordance for the ability to smell androstenone is reported to be considerably higher among identical than fraternal twins (100% and 61%, respectively). In addition, it is known that a human odorant receptor, OR7D4, is selectively activated in vitro by androstenone and the related odoros steroid androstadienone (androsta-4,16-dien-3-one). Our results showed that among all of the 74 ORs with genetic variations, only OR1B1 responded to androstenone. OR1B1, as a segregating pseudogene, displays both functional and nonfunctional alleles in human which makes it as excellent candidate to explain variation of androstenone perception in human population.

A search for polymorphisms in OR1B1 in SNP databases determined SNPs in this receptor, with three occurring at frequencies greater than 25%. We investigated the ligand specificity of OR1B1-574, OR1B1-688 and OR1B1-789 receptor variants in recombinant expression systems with androstenone as a suitable ligand for OR1B1-WT. OR1B1-574 is a mutant form of OR1B1 that converts the active gene of OR1B1 to pseudogene (Arginine change to termination amino acid) with a frequency of 33%. OR1B1-688 and OR1B1-789 are missense SNPs. OR1B1-688 and OR1B1-789 did not show any significant difference in evoke responses to androstenone and testosterone in comparison with OR1B1-WT; however, OR1B1-574 showed that mutations on SNP in position 574, which change amino acids into extracellular loop 2 and convert OR1B1 to pseudogene, severely impair OR1B1 function. It should be noted that OR1B1 responded to androstenone and, in addition, also responded to 3-hydrtoxy-2-methyl-4-pyran and Calone, thus cannot be regarded as a specific receptor for androstenone, but the other 73 ORs did not respond to this odorant. This result could provide a link between polymorphism in the OR1B1 gene (as SPGs) and phenotypic variation. Also, our results demonstrated that one odorant can activate more than one receptor. So, under the assumption of a multi-receptor response to androstenone, androstenone hyposmia may reflect total lack of, or a reduced number/density of, particular olfactory receptors. Our results, however, do not rule out specific androstenone hyposmia as a helpful key to consider the genetic basis of odor discrimination.

Despite ω-cyclopentadecalactone (Pentadecanolide) being known as an odorant related to specific anosmia, no olfactory receptor(s) were presented as a deorphanized receptor for the detection of pentadecalactone. Since the early studies it has been shown that the incidence of specific anosmia to pentadecalactone within families follows a simple Mendelian inheritance pattern and the reason of specific anosmia explained as an inheritable defect in one of the olfactory receptor proteins. Here we presented OR10Q1 as one OR in the CNV group that responded to ω-cyclopentadecalactone as an odorant in the musk group. The comparative analysis indicates that the genetic variations of OR10Q1 and OR4K2 as deorphanized receptors for pentadecanolide are different in comparison with specific anosmia rates of pentadecanolide in the human population. Among all of the 76 olfactory receptors, including SPGs and CNVs, three olfactory receptors in the CNV group responded to the musk group. With the exception of OR4P4 that responded to Globalide with a 40% deletion rate in the human population, OR10Q1 and OR4K2 responded to Pentadecanolide. It could be concluded that at the very least segregating pseudogenes do not play an effective role in the phenotype variation of Pentadecanolide and Globalide musky odorants. Also, affinity of OR10Q1 to Pentadecanolide was deliberate with mutagenesis by overlap extension PCR. The mutated OR10Q1 was produced according to a unique single nucleotide variation with MAF>10%. We investigated the ligand specificity of OR10Q1-540 (mutated variant) and OR10Q1 (wild type) receptor variant in vitro with Pentadecanolide as a suitable ligand for OR10Q1. The mutated variant does not show any significant difference in comparison to OR10Q1-WT.

There is limited knowledge about most odorants in terms of different kinds of anosmias. This lack of data about anosmia leads to some difficulties finding a relation between genetic variation and odorant perception in different populations. However, some particular odorants (isovaleric acid, 1-pyrroline, Trimethylamine, Isobutyraldehyde, 5α-androst-16-en-3one and ω-pentadecalactone) were determined as primary odorants. Among the identified primary odorants we determined some ORs related to isovaleric acid, Isobutyraldehyde, 5α-androst-16-en-3one and ω-pentadecalactone. The genetic variation rates and the possible perceived variations are compared in Table A:

TABLE A

Genetic variation rates of olfactory receptors in comparison with anosmia occurrence

| ORs | Genetic variation [%] | Ligands | Primary odor | Anosmia occurrence [%] |
|---|---|---|---|---|
| OR1B1 | 33 | 5a-androst-16-ene-3-one | urinous | 47 |
| OR4K2 | 54 | isobutyraldehyde | malty | 36 |
| OR10Q1 | 0.6 | w-pentadecalactone | malty | 12 |
| OR12D2 | 37 | Isovaleric acid | sweaty | 3 |

The comparative analysis indicates that the genetic variation of OR1B1 may play a role in the urinous anosmia while the genetic variations of OR4K2 (54%), OR10Q1 (0.6%) and OR12D2 (37%) are different in comparison with the specific anosmia rates of musky (12%), malty (36%) or of sweat odor (3%). However, this analysis is based on the hypothesis of the theory "specific anosmia and the concept of primary odorants".

According to the present results, OR2L8 responded to Ysamber K and Timbrol. According to results of the experiments, 25% (7 of 32) of odorants responded to more than one OR as segt out in Table B:

TABLE B

Odorants that respond to more than one OR

| Odorant | Olfactory Receptor |
|---|---|
| Ysamber K | OR2L8; OR4K5 |
| Octadecanal | OR4C16; OR5L1 |
| Beta-damascone | OR5L1; OR4C3 |
| Hexanal | OR8D2; OR10A6 |
| Muguet Alcohol | OR8D2; OR10A6 |
| 2,4,6-trichloranisole | OR52B4; OR4E2 |
| 3-phenylpropyl aldehyde | OR4E2; OR4K2 |

In relation to the above point, that odorants are detected by the collection of ORs and taking into consideration that humans that have a special combination of ORs with vast interindividual variability, it could be considered that the olfactory systemproduces an enormous potential for phenotype variation for odorant perception in terms of different kinds of anosmias. Also, it seems that the interpreting of SNPs in individual ORs cannot conduct a prediction plane about the conception of odorants in the human population.

According to the aim of our large-scale investigation about the ORs with genetic polymorphism, we provided more deorphanized receptors to get a better understanding of the relation between olfactory receptors and chemical components. In our study we screened approximately 20% of human repertory olfactory receptors as SPGs and CNVs, so it could be expected that in the future the number of olfactory receptors that respond to similar odorants would be increased. Also, the failure of a specific odorant receptor to respond in this assay must be interpreted with caution because it may reflect a failure of the odorant receptor to be functional in the assay rather than a lack of sensitivity to the tested odor.

To sum up, with regard to the total number of deorphanized olfactory receptors, it should be noted that despite starting with roughly similar numbers of SPGs and CNVs, we identified agonists for over two times more SPGs than CNVs. These results are in agreement with current knowledge that every human individual is characterised by a different combination of such segregating pseudogenes, which makes a genotypic diversity in human population, and it is indicative of the important role of SPGs in genetic variation in relation to different anosmias. With regard to recent findings about specific combinations of intact and inactive alleles with CNV and SPGs in individual humans, which leads to each person having highly personalised barcodes of functional olfactory receptors, and in connection with our deorphanized receptors and different odorants between SPGs and CNVs, makes it easier to explain the variation patterns of odorant conceptions.

Broadly and Narrowly Tuned Olfactory Receptors

Some olfactory receptors are "generalists" which bind a variety of ligands and reveal broad recognition abilities and large plasticity of their binding cavity while others are reported as "specialists" that are narrowly tuned to a small number of ligands. Results of current study showed that 77% (14/18) of our receptors are broadly tuned and do not respond only to one special odorant or chemical component. The sense of smell allows us to perceive volatile chemicals present in our environment. The almost unlimited numbers of odorant molecules have to be accurately understood by the human nose. To this end, our sense of smell has to adapt to concept wide variety of odorants and chemical components by limited numbers of active ORs. We perceive odors through a combinatorial code involving less than 400 receptors. Then, as this study showed, many of our receptors should probably be broadly tuned and do not respond only to specific odorants. The plasticity of the binding cavity of OR allows different ligands to interact with various residues and odorant receptors could be adapted to different chemical structures. So, broadly tuned OR makes it possible to explain the perception of unlimited odorants by limited numbers of functional receptors.

It should be noted that ORs are presented as responsible for specific odorants (4/18) and could respond to more chemical components but because of the small number of odorants that we used in our study we were not able to show other possible odorants.

Scent and Chemistry

The structure-odor relationship is complicated and some description of odor like smell or quality of odor is usually unpredictable from its molecular structure. It is suggested that an olfactory receptor detects a part of an odorant molecule, rather than the entire shape of a molecule. The experimental data, in accordance with this view, shows that most odorants respond to one OR have the same functional groups. It seems that chemical functional groups and carbon atom numbers (CAN) are more important in the detection of odoranta by an OR rather than the similarity of chemical structures. Also, it is known that functional groups roughly determine the specifications of odorants but it should be noted that only the presence of functional groups cannot explain the odor of molecules.

The experimental results of the potential link between individual ORs and perceived odor characteristics led to a classification into three different groups.

(a) ORs that only responded to one odorant: OR4X2, OR4C16, OR511 and OR10Q1 responded to 2-aminoacetophenone, aldehyde C18, Octanal and Pentadecalactone respectively. Second, ORs recognised odorants that share special chemical descriptors such as functional groups or odor quality like OR2L8 and OR4K5 that only responded to the amber odorant group or OR5L1 that responded to odorants with fruity properties. In the experiments, 64% (9/14) of ORs that responded to more than one odorant have similar functional groups or the same odor quality. Carbon atom numbers (CAN) are known to be an important odorant descriptor from a number of studies.

(b) 35% (5/14) of ORs that responded to more than one chemical component, responded to odorants with similar CAN. OR4E2 responded to odorants with CAN between 9 and 11; OR2L8 and OR4K5 responded only to odorants with CAN between 15 and 17. Odorants with a low or high number of CAN (6<CAN<12) consist of allow number of deorphanized odorants. It should be noted that most of the known odorants such as anosmia like musks, ambers or androstenone have high numbers of CAN.

(c) ORs responded to odorants that do not share a common descriptor. OR52B4, OR4P4, OR4K2 and OR4C3 are located in this category. With the exception of OR12D2 we could not find any other OR that only responds to odorants with similar chemical shapes. But it should be noted that all ligands of OR12D2 belong to the acid carboxylic group and share the same functional groups. For example, among all of the 18 deorphanized ORs just OR12D2 responded to structurally related odorants with similar functional groups:

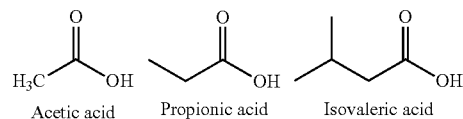

Acetic acid    Propionic acid    Isovaleric acid

In a parallel study all of the ORs were screened that responded to one of the musk odorants (OR4P4, OR4K2 and OR10Q1) with other similar odorants in the musk group comprising the following species:

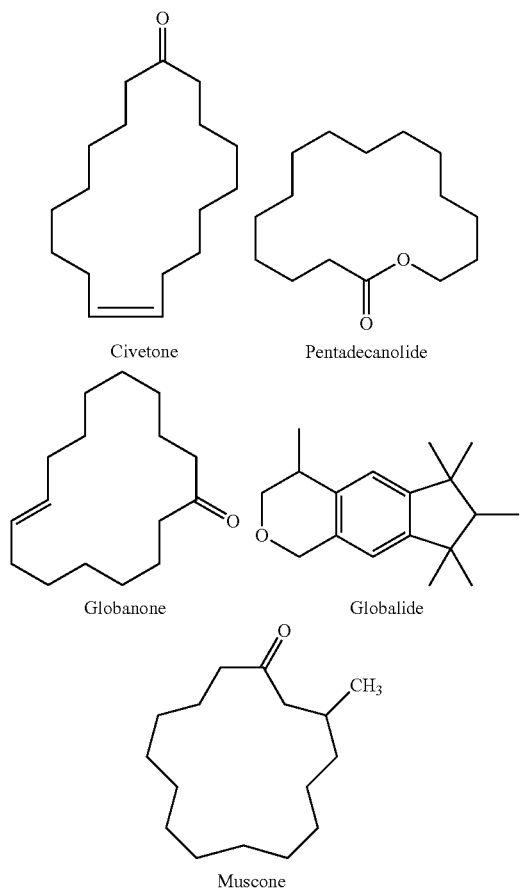

But in this case one could not detect any significant relation between chemical structure similarities and responses of OR in the musk group.

With regard to our results, although the third group that responded to unrelated odorants cannot be excluded, in most cases these findings are in agreement with the idea that individual ORs might have reacted and responded to particular odor descriptors like chemical groups, odor qualities (odorant perception as minty, fruity, woody or musky) or CAN in comparison to the entire shape of odorant chemical structures. Also, among the odorant descriptors, it seems that functional groups are more important than carbon atom numbers.

In the course of present invention it was found that one OR can recognise multiple odorants with related functional groups while one odorant is recognised by different receptors. For example, OR8B4 and OR8D2 are activated by Muguet alcohol, and alcohol C6 elicited a response in OR8D2 and OR10A6. Aldehyde C6, alcohol C6, Graniol and Octanal are found to act as ligands for OR2W1; Graniol is also discovered as a ligand for OR2M7. OR51E2 and OR51L1 are found to be receptors for propionic acid and n-hexanoic acid, respectively. In addition, OR11H4, OR11H6 and OR11H7 were identified in a genetically based study as receptors for isovaleric acid. Although not many odorants could activate more than one OR but in combination with previous deorphanization results it is obvious that the relation between ORs and odorants is complex and that one odorant could activate with more than one receptor, according to the hypothesis known as "combinatory code", which allows for the perception of unlimited odorants by different combination of ORs.

5α-Androst-16-En-3One (Urinous) and ω-Pentadecalactone (Musky) Molecules

5α-androst-16-en-3one and ω-pentadecalactone were chosen as reference odorants for urinous and musky odorants respectively. These two odorants have molecular weights in the same general range and a similar orientation of functional groups and also have the same molecular thickness. But the androstenone molecule is longer and narrower, whereas the pentadecalactone is shorter and wider. It is suggested that these differences is origin of differentiate between urinous and musky odorants in the human olfactory organ. In our experiments we found different receptors to be responsible ORs for androstenone and pentadecalactone. The separation of responding ORs for these two primary odorants could be part of a possible discriminatory mechanism.

Also, in a parallel study, it was shown that OR1B1 (which deorphanized for androstenone) responded to testosterone as a steroid hormone from the androgen group. Androstenone is a steroid and a metabolite of testosterone. Testosterone and androstenone have similar general chemical structures with the same number of CAN.

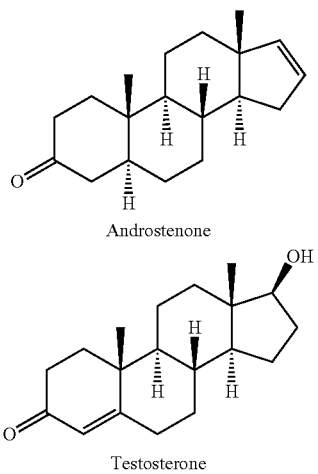

Androstenone

Testosterone

Interestingly, testosterone secreted partly by adrenal glands. The HORDE data base shows expression of OR1B1 in adrenal glands. Also, it has been shown that OR1B1 is expressed in prostate and brain tissues.

EXAMPLES

A. Material and methods
A1. DNA Constructs and Plasmids

Human ORs (SPGs/CNVs) were amplified from human genomic DNA by PCR using specific primers, which amplify the complete open reading frame and contain restriction sites(EcoRI, NotI, ApaI and SalI) for further subcloning into pCI expression vector (Invitrogen). Amplified ORs were cloned in multiple cloning site of pCI vector contain with Rho-tag. PCR reactions were done with 100 ng genomic DNA and specific primers for human olfactory receptors. The generated plasmid was verified by sequencing. Primers were designed with Primer3plus software, with parameters including of melting temperature (Tm) between 55 and 650 C, GC-content between 30% and 70% and length from 18 to 28 bp. The restriction site was chosen identical with the restriction site in pCI-vector. It was controlled with the Webcutter 2.0 software to ensure that the restricted nucleotide site is not identical with any nucleotide region inside the target gene.

The expression cofactor RTP1 was co-transfected to support the expression of recombinant ORs on the cell surface. The other cofactors Gα15, Myr-Ric8A, and HSC70 were also co-transfected for augmentation of olfactory signals which are produced by OR activations. Myr-Ric8A was generated by using Ric8A primer including Myr site (Yoshikawa, Touhara 2009) and cloning the PCR products into a pcDNA3 vector. Forward and reverse primers used in construction of Myr-Ric8A were as follow:

(SEQ ID NO: 2)
gcatatGAATTCACCATGGGTAGCAACAAGAGCAAGCCCAAGGATGCCAG
CCAGCGGATGGAGCCCCGGGCGGTTGC as forward primer included restriction site of EcoRI and (SEQ ID NO: 3)
gcatatGCGGCCGCTCAGTCAGGGTCCGAGTCAGGGT as reverse primer with NotI restriction site.

FIG. 1 shows the cloning of ORs.
A) pCI expression vector (Invitrogen) including Rho-tag as a leader peptide sequence.
B) ORs were amplified with 100 ng genomic DNA and specific primers for human olfactory receptors by PCR. The restriction site was chosen identical with the restriction sites in pCI-vector.
C) The generated recombinant plasmids were verified by sequencing.
A2. Mutagenesis by Overlap Extension PCR Mutations were introduced for OR1B1 and OR10Q1 by Overlap Extension PCR (OEP). The following Table 2.1 shows primers for site-directed mutagenesis of OR1B1 and OR10Q1 genes. Flanking primers in combination with internal primers provided mutated gene segments, Full length primers included EcoRI and NotI restriction sites for further cloning into pCI expression vector. Site-directed mutations were selected for base of minor allele frequency of nucleotide.

TABLE 2.1

Primers for site-directed mutagenesis

| Flanking Primer | Internal primers | Point of Mutation and Frequency |
|---|---|---|
| OR1B1 Forward(Fwd): GCATATGAATTCATGATGAGCTTTGCC CCTAATG (SEQ ID NO: 4) Reverse(Rev): GCATATGCGGCCGCGGGGTCTACCTTC ACCCATTC (SEQ ID NO: 5) | OR1B1-688(Fwd): GAATTGGGGCCACTATTCTACG (SEQ ID NO: 8) (Rev): CGTAGAATAGTGGCCCCAATTC SEQ ID NO: 9) | G (standart) → A (mutation) Nucleotide: 688, MAF: 0.39 |
| | OR1B1-574(Fwd): CCGGCCACTTCTGTGAGCCTCTTG (SEQ ID NO: 10) (Rev): CAAGAGGCTCACAGAAGTGGCCGG (SEQ ID NO: 11) | C (standart) → T (mutation) Nucleotide: 574, MFA: 0.31 |
| | OR1B1-789(Fwd): CACCTCATTTGGGTCTACTTCC (SEQ ID NO: 12) (Rev): GGAAGTAGACCCAAATGATGGTG (SEQ ID NO: 13) | T (standart) → G (mutation) Nucleotide: 789, MAF: 0.25 |
| OR10Q1 Fwd: gcatatGTCGACATGCCTGTGGGGAAA CTTGT (SEQ ID NO: 6) Rev: gcatatGCGGCCGCTCAGTTGGCGTCA GAGGCTG (SEQ ID NO: 7) | OR10Q1-540(Fwd): GGAAATCAATCACTTCCTCTGC (SEQ ID NO: 14) (Rev): GCAGAGGAAGTGATTGATTTCC SEQ ID NO: 15) | C (standart) → T (mutation) Nucleotide: 540, MAF: 14% |

Figure 2:
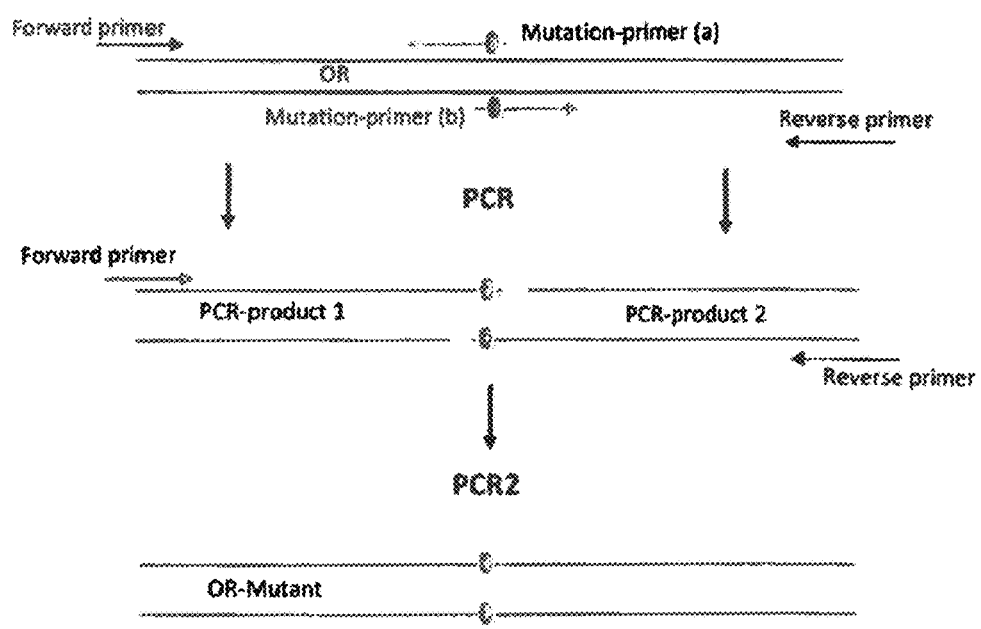
FIG. 2 schematically illustrates generation of OR1B1 and OR10Q1 mutants by Overlap Extension PCR.

In mutagenesis by overlap extension PCR method, initial PCRs provided mutated gene segments, with overlapping complementary 3' ends carrying desired point mutation that were then mixed and used as template for a subsequent PCR to generate the full-length product. Overlapping strands of these intermediate products hybridize at this 3' region in a subsequent PCR and are extended to generate the full-length product amplified by flanking primers; this shown in FIG. 2. Full length primers included restriction sites for further cloning into pCI vector. The nucleotide sequence of the mutants was verified by sequencing. In more detail the primers were obtained according to the following procedure:

First PCRs generate overlapping gene segments that are then used as template DNA for second PCR to create a full-length product. Internal primers generate overlapping, complementary 3' ends on the intermediate segments and introduce nucleotide substitutions for site-directed mutagenesis. Overlapping strands of these intermediate products hybridize at this 3' region in a subsequent PCR and are extended to generate the full-length product amplified by flanking primers.

A3. Odorant Library

Odorants which are related to specific anosmia were used for odorant explorations for OR expressions. These 66 odorants were divided to deferent groups according to chemical structures and smelling. Odorants contained in each mixture are shown below.

(1) Musk Group:
(1.1) Galaxolide, (1.2) Globalide, (1.3) Globanone, (1.4) Helvetolide, (1.5) Isomuscone, (1.6) ω-cyclopentadecanolide, (1.7) Muscone, (1.8) Musk Ketone, (1.9) Oxonate, (1.10) Traseolide, (1.11) Macrolide Supra.

(2) Amber Mixture
(2.1) Ambroxan, (2.2) Cedramber, (2.3) Karanal, (2.4) Timberol, (2.5) Ysamber K.

(3) Ketone Mixture
(3.1) 2-Aminoacetophenone, (3.2) 2-Butanone, (3.3) 3-Hydroxy-2-Methyl-4-Pyran-4-one, (3.4) 5α-Androst-16-en-3-one (Androstadien-3-one), (3.5) Hedion, (3.6) α-Ionone, (3.7) 1-Octen-3-one, (3.8) Civetone, (3.9) Methyl naphthyl keton B, (3.10) Methylhexylketon, (3.11) β-Damascone, (3.12) Calone (4) Carboxylic Acids Mixture
(4.1) Acetic acid, (4.2) Isobutyric acid, (4.3) Isocaproic acid, (4.4) Isovaleric acid, (4.5)NHexanoic acid, (4.6) Propionic acid (5) Alcohol Mixture
(5.1) Alcohol C6, (5.2) Alcohol C9, (5.3) Anisylalcohol, (5.4) Benzylalcohol, (5.5) Cinamylalcohol, (5.6) Muguetalcohol, (5.7) Phenylethylalcohol, (5.8) Phenylpropylalcohol, (5.9) Geraniol (6) Aldehydes-Lactones Mixture
(6.1) 3-Phenylpropionaldehyde, (6.2) Aldehyd C6, (6.3) Aldehyde C12, (6.4) Aldehyde C14, (6.5) Aldehyde C18, (6.6) Anisic Aldehyde, (6.7) Benzaldehyde, (6.8) Heptanaldehyde, (6.9) Hydratropicaldehyd, (6.10) Isobutyraldehyde, (6.11) Octanal, (6.12) Trans-2-Nonenal (7) Mixture of Other
(7.1) 2,3-Butanedione, (7.2) 2-4-6-Trichloroanisole, (7.3) Geosmin, (7.4) L-Carvone, (7.5) Lyral, (7.6) Sandranol, (7.7) 2-Isobutyl-3-Methoxypyrazin, (7.8) 1-Butanthiol, (7.9) Methyldisulfide, (7.10) Skatole, (7.11) Ozonil (7.12).

The preferred odorants belong to the group formed by ketones, aldehydes, lactones, carboxylic acids and odorous steroids. Odorant stock solutions were prepared in dimethyl sulfoxide (DMSO). Chemical component were diluted with Ringer's solution to concentration for Ca-imaging (final DMSO concentration was maximum 0.2%).

A4. Cell Culture and Transient DNA Transfection

HEK293 cells were cultivated in Petri dishes (Ø35 mm) as previously described (Benbernou et al. 2007). We grow up HEK293 cells in culture medium containing standard DMEM with 10% heat-inactivated fetal bovine serum, 2 mM L-glutamine, 100 units/ml penicillin, and 100 units/ml streptomycin in a humidified atmosphere (37° C., 5% CO2). After 2-3 days, the transfection process was carried out, whereby the cell culture was 70-80% confluent. The calciumphosphate method was applied to transfect DNA plasmid transiently in HEK293 cells in case of Ca-imaging method.

Calcium cations and phosphate anions created crystal precipitations coupled with DNA which could invade into the cells through endocytosis. Cells were transiently transfected with plasmid DNA which consists of pCI expression vector and PCR-amplified full-length cDNA of olfactory receptors candidates, and also Gα15, RTP1, Myr-Ric8A, HSC70, and m-Cherry as cofactors. The precipitation could be created after 15-20 min, with dropping the transfection solution on HEK293 cells. Before measuring by Ca-imaging cells were incubated 48-60 hours at 370 C, 5% CO2. Cationic liposome-mediated transfection method was applied to transfect DNA plasmid transiently in HANA3A cells in case of CRE-Luciferase and CRE-SEAP assays.

HANA3A cells were plated in 96 well plate covered with poly-D-lysine at roughly density about 4000 cells/well (in 50 μl volume). After 24 h incubation (370 C/CO2), Table 2 shows the additives added in two different tubes (Scale according to one well):

TABLE 2

| Additives |
|---|
| Tube a) 52 ng receptor plasmid |
| 20.8 ng pCRE-Luci plasmid |
| 10.4 ng pSV40-Renilla |
| DMEM (no serum) 5 μl per well. |
| Tube b) 0.15 μl Fugene transfection reagent (according to protocol) |
| DMEM (no serum) 5 μl per well |

To prepare the transfection complex, we mixed solution (a) and (b) together and incubate them for 15-20 min at room temperature and in last step 45 μl DMEM (with 5% FBS) was added to the "ab" mixture. After aspiration media from cells in the 96 well plates 50 μl of DMEM (with 5% FBS and AB mixture) was added to each well.

A5. Ca-Imaging

Calcium imaging of the transfected HEK293 cells was done by using chambers determinate an inverted microscope (Olympus; IX70) using a 10× objective (CPIanFL N Olympus). Fluorescence emission was determined every 4 s by using a CCD camera (Charge Coupled Device, C9100 Hamamatsu). The capillary tube which was responsible to supply odorants was generated closely above the cells. The columns filled with odorants, DMSO and ATP. Odorants were manually monitored to drop each 4-5 s to transfected cells. Solutions with drop wise form spread on HEK293 cells in 35 mm dishes.

In experiments, Fura-2 Acetoxymethylester (Fura-2/AM) was applied. The non-polar Fura2/AM is fluorescent but not yet calcium-sensitive. Once diffuses into cell plasma, Fura-2/AM is hydrolyzed to Fura-2 which is calcium-sensitive and functions as Ca2+ chelator. Regardless of the presence of calcium, Fura-2 emits at the wavelength of 510 nm. Once Fura-2 binds to free intracellular Ca2+ in cell plasma, its ratio of excitation at wavelengths of 340 nm and 380 nm is changed and correlated to the amount of intracellular Ca2+. According to this feature, the analysis of 340/380 nm excitation ratio for Fura-2 allows to quantify intracellular calcium levels.

In preparation for Ca-imaging measurements, transfected HEK293 cells were added 3 it Fura2/AM (3 μM) and incubated 30-45 min at 370 C, 5% CO2. After this step, experiments were carried out in a dark condition (Fura-2 is light-sensitive). After the incubation, medium of cell culture was replaced with 2 ml Ringer's solution.

The transfection rates of cells controlled with transfected m-Cherry plasmid. Transfected cells by m-Cherry could be observed as red cells under fluorescence of microscope (emission maximum at 610 nm)

A6. Stimulation and Screening with Odorants

Odorants were freshly prepared with DMSO as 1 M stocks solutions. Six mixtures (200 μM each chemical) were applied to cells sequentially (20 s each mixture/30 s Ringer). Those ORs tested with single odorants that had generated a response to odorant mixture group previously. Odorants were prepared in 100-200 μM concentration.

Ringer's solution was used for washing cells between measuring by two different odorants. Positive response was determined by the timing of the response, the strength of the response (more than twofold higher than the noise amplitude of the baseline), and the shape of the response curve (sharp rise in curve with gradual recovery). The typical shape of response curves was established by observing responses to repeated stimulation with 200 μM of odorants. After testing with single odorants at 100 μM, stimulating odorants were often retested at 200 μM concentrations. To confirm the result of every receptor that produced a significant response curves, the experiment was repeated for twelve times. Finally, cells were exposed to ATP (0.25 mM) which could activate P2Y receptor channel and induce Ca2+ influx into cells.

A7. Strategy of Screening

For screening ORs with all 66 odorants, they were classified into 7 different chemical groups. Odorants were applied in two steps, during the first one; ORs were screened by odorant groups and in the second step particular odorants were applied for deorphanization. In first step of ORs screening, odorant groups were applied for ORs during three different times of measuring. ORs that responded to same odorant groups at least for two times were selected for next step of screening with particular odorants in same responded odorant group. In the second step, if the OR after three times of measuring responded significantly to particular odorants, it would be selected for more measuring otherwise it would be excluded from the experiments. To get final conformation of deorphanized olfactory receptors they were repeated six times during two sets of experiments that each set was including of three measurements. In this study those of ORs were presented as deorphanized receptors that during all of sets showed significant responses ($P<0.05$).

A8. CRE-Luciferase

The Dual-Luciferase® Reporter (DLR™) Assay and Dual-Glo™ Assay enable the sequential measurement of both firefly and renilla luciferases from one sample. Odorant receptor activation leads to an increase in intracellular cAMP; we used CRE-luciferase to measure this change. renilla luciferase driven by a constitutively active SV40 promoter (pRL-SV40; Promega) served as an internal control for cell viability and transfection efficiency. At the end data were normalized to renilla activity levels by dividing the value obtained for firefly luciferase by the renilla luciferase value.

ORs responded by Ca-imaging with seven separate odorant mixtures formed from 66 odorants. Odorants were applied at 5 different concentrations (50 μM, 100 μM, 150 μM, 200 μM, 250 μM, 300 μM) and all ORs that did not show activity with Ca-imaging were eliminated. We used Dual-Gb™ Luciferase Assay System (Promega) for the luciferase assay in order that it is described below.

1. Transfected HANA3A cells on poly-D-lysine-coated 96 well plates are ready for stimulation after 24 h. The cells in each well should be 50-80% confluent at the time of stimulation.
2. Replace DMEM medium with CD293 (chemically defined medium) and incubation the plate for 30 min at 370 C and 5% CO2.
3. Add 25 µl of odorant solution diluted in CD293 and incubation 4 h at 370 C and 5% CO2.
4. Incubate the plate with firefly luciferase buffer (20 µl per well) in 10 min at room temperature.
5. Measuring by plate reader (Luminometer).
6. Add second buffer (renilla/20 µl per well) and incubation in 10 min at room temperature.
7. Measuring by plate reader (Luminometer).
8. According to manufacturer's protocols for measuring luciferase and renilla activities, calculate normalized luciferase activity with using the formula (Ln-Lmin)/(Lmax-Lmin), where Ln is the luminescence of firefly in response to the odorant, L min is the minimum luciferase value on a plate, and L max is the maximum luciferase value on plate.

A9. CRE-SEAP Assay

Secreted embryonic alkaline phosphatase (SEAP) is a reporter widely used to study promoter activity or gene expression. It is a truncated form of human placental alkaline phosphatase (PLAP) by deletion of the GPI anchor. Unlike endogenous alkaline phosphatases, PLAP is extremely heat stable and resistant to the inhibitor L-homoarginine. SEAP is secreted into cell culture supernatant and therefore allows determining reporter activity without disturbing the cells For the SEAP assay, cells from each well were cotransfected with Gα olf, Ric8b, RTP1, OR and a pCRE-SEAP plasmid in order that coming bellow. The protocol of CRE-SEAP assay provided kindly by L. Buck.

Day 1: Cell Seeding

Seeding the HEK293 cells in DMEM (10% fetal calf serum), 6000-7000 cells per well.

Day 2: Transfect Cells and Add Test Ligands
1. For 1 well, the followings are added in an eppendorf tube (scale according to number of wells needed and use excess to cover loss during pipetting):

| OR | CRE-SEAP plasmid | Gα olf | RTP1 |
|---|---|---|---|
| 25-50 ng | 25 ng | 25 ng | 25 ng |

Transfection with Lipofectamine:
Per Well:
1—Master mix(OR+CRE-SEAP+Gα olf-RTP1)+25 µl opti-Mem medium
2—Lipofectamine (0.2 µl per well)+25 µl OptiMem medium (wait for 5 min please)
1+2=Incubate 15-20 min at room temperature
Whole the mixture (1+2) added to each well (without medium replacing)
3—Incubated at 37 for 24 h.

Day3

24 h after transfection, Medium will be replaced by 200 µl of serum free DMEM medium containing different agonists (odorants).
1 Incubated for 6 h at 370 C.
2 200 µl of media from each well will be transferred to a new plate (96 well plates).
3 Heating 650 C for 30 min.
4 100 µl supernatant from each well will be transfer to new 96 well plates (Black well plates) & adding 100 µl SEAP Buffer (0.5 mM MgCl2, 1M diethanolamine, 1.2 mM 4-MUP, 10 mM Homoarginine, pH=10) to each well.
5 Incubated for 10 min at 370 C.
It should be noted that, assay becomes time-sensitive after addition of Reaction Buffer.
6Read plate for fluorescence at wavelength: Excitation 335 nm & Emission 449 nm (the name of program on Packard tetra plate reader system is CRE-SEAP).

A10. Immunohistochemistry

Immunoassay systems were used to consider the expression of olfactory receptors in HEK293 cells and expression on the cell surface. For immunohistochemistry studies HEK293 were grown on polylysine-coated coverslips (80-100 µm thickness; Menzel Gläser, Germany). After the transfection of the HEK293 cells, coverslips were fixed by incubation in 3% paraformaldehyde in Ringer's solution containing 10 mM glucose at room temperature for 30 min. Cells were permeabilized with 0.1% Triton X-100 in PBS containing 1% cold-water fish skin gelatin (Sigma) and incubated with Rho-tag antibody 4D2 (primary antibody) in PBS/gelatin/Triton X-100 (1:200). After washing, coverslips were incubated with fluorescently labeled secondary antibodies (488-Goat-Anti mouse 1:1000) and mounted in Pro-Long Antifade (Molecular Probes). All fluorescence images were obtained with a confocal microscope (LSM510 Meta; Zeiss). Also to investigate of OR expression in cell surface of the cells we tried to live cell-surface staining plasma membrane.

For live cell-surface staining Plasma membrane expression of N-terminally tagged Rho-tag was assessed using the primary anti-rhodopsin antibody, 4D2 in staining solution (1:100, 1 h incubation on ice) and HEK293 cells were incubated with 4D2 anti body for 30 min. After aspiration of staining solution including 4D2 anti body, cells would be incubated with second antibody on ice. Labeled OR protein was visualized by using a 488-Goat Anti-Mouse secondary antibody (1:200, goat-anti-mouse) and confocal microscopy (LSM510 Meta; Zeiss, 100_ HCXPL APO oil immersion).

A11. Data Analysis

The graphs of individual cells from Calcium imaging data (fluorescence intensity vs time in seconds) done by using Excel software (Microsoft). Responses were analyzed by the fractional change in fluorescence intensity: $\Delta F/F_o$ or $(F-F_o)/F_o$, where F is intensity at each time point after stimulation and Fo is the value of emitted fluorescent light before the stimulus application (baseline). To determine significant cell responses in regard of OR activations to a particular odorant, the statistical chi-square test (four fields) was applied. P-value <0.05 was considered as significant result.

B. Results

B1. Identification of SPG and CNV OR Candidates

By the HORDE data base, in total around 60 olfactory receptors were presented as SPGs. In the first approach, we attempted to clone all of the 60 SPGs and in most cases we selected ORs as SPGs with high SNP variation. After cloning, recombinant plasmids were sequenced and results were compared with the gene data bank of the NCBI data base. Those ORs determined as pseudogene were excluded from experiments. In the end 40 SPGs were selected for deorphanization shown in Table 1:

TABLE 1

Segregating Pseudogenes

| OR family | Olfactory receptors | Chromo-some | SNP | MAF |
|---|---|---|---|---|
| 1 | OR1B1 | 9q | a nonsynonymous SNP rs1476860 (AA change=R/*) | A = 0.333/ 727 |
|  | OR1S1 | 11q | a nonsynonymous SNP in a highly conserved amino-acid (rs 1966834) | G = 0.496/ 1083 |
|  | OR1E3P | 17p | a polymorphism of C-> del at position 54 (rs11377766) | T = 0.120/ 263 |
| 2 | OR2F1 | 7q | a polymorphism in a highly conserved amino-acid (rs2072164) | A = 0.224/ 489 |
|  | OR2L8 | 1q | a nonsynonymous SNP in a highly conserved amino-acid (rs4925583) | T = 0.385/ 843 |
|  | OR2I1 | 6q | a nonsynonymous SNP rs2394517 (AA change =*/Q) | T = 0.021/ 45 |
|  | OR2S2 | 9p | a nonsynonymous SNP in a highly conserved amino-acid (rs2233563) | G = 0.038/ 38 |
|  | OR2AG1 | 11 | a nonsynonymous SNP in a highly conserved amino-acid (rs11828041) | T = 0.340/ 742 |
| 4 | OR4X1 | 11p | a nonsynonymous SNP rs10838851 (AA change=Y/*) | G = 0.167/ 364 |
|  | OR4X2 | 11p | a nonsynonymous SNP rs7120775 (AA change=Y/*) | T = 0.277/ 605 |
|  | OR4C16 | 11q | a nonsynonymous SNP rs1459101 (AA change=Q/*) | G = 0.259/ 566 |
|  | OR4E2 | 14q | a nonsynonymous SNP in a highly conserved amino-acid (rs2874103) | G = 0.026/ 57 |
| 5 | OR5D13 | 11q | a nonsynonymous SNP in a highly conserved amino-acid (rs297118) | G = 0.286/ 625 |
|  | OR5H6 | 3q | a nonsynonymous SNP in a highly conserved amino-acid (rs9289584 and rs9853887) | T = 0.359/ 784 |
|  | OR5AL1P | 11q | a polymorphism of 2 bp del at positions 468-469 (rs10633383) | C = 0.098/ 213 |
|  | OR5L1 | 11q | a nonsynonymous SNP in a highly conserved amino-acid (rs12790505) | C = 0.039/ 85 |
|  | OR5R1 | 11q | a nonsynonymous SNP in a highly conserved amino-acid (rs7111634 and rs6591324) | A = 0.244/ 534 |
| 6 | OR6J1 | 14q | a nonsynonymous SNP in a highly conserved amino-acid (rs3751484) | T = 0.167/ 384 |
|  | OR6Q1 | 11q | a polymorphism of C->del at position 685 | - = 0.132/ 289 |
| 7 | OR7C2 | 19p | a nonsynonymous SNP in a highly conserved amino-acid (rs11883178) | A = 0.0.35/ 76 |
| 8 | OR84 | 11q | a nonsynonymous SNP in a highly conserved amino-acid (rs4057749) | G = 0.266/ 580 |
|  | OR8K3 | 11q | a nonsynonymous SNP in a highly conserved amino-acid (rs960193) | T = 0.238/ 520 |
|  | OR8G1 | 11q | a nonsynonymous SNP rs4268525 (AA change=Y/*) | C = 0.500/ 1092 |
|  | OR812P | 11q | a nonsynonymous SNP T->C at position 190 (AA change=*/R) |  |
|  | OR8D2 | 11q | a nonsynonymous SNP in a highly conserved amino-acid (rs2512219) | T = 0.238/ 520 |
| 10 | OR10AB | 11p | a nonsynonymous SNP in a highly conserved amino-acid (rs4758258) | A = 0.221/ 482 |
|  | OR10X1 | 1q | a nonsynonymous SNP rs883362 (AA change=W/*) | C = 0.465/ 1016 |
|  | OR10C1 | 6p | a nonsynonymous SNP rs17184009 (AA change=Q/*) | T = 0.025/ 55 |
| 12 | OR12D1P | 6P | a polymorphism of 16 bp del at positions 556-572 |  |
|  | OR12D2 | 6P | a nonsynonymous SNP in a highly conserved amino-acid (rs2073153) | C = 0.370/ 809 |
| 13 | OR13C7P | 9P | a polymorphism of 2 bp insertion (AA) at positions 435-436 |  |
| 51 | OR51G1 | 11p | a nonsynonymous SNP in a highly conserved amino-acid (G->A at position 371, R130H) |  |
|  | OR51B2 | 11p | a nonsynonymous SNP in a highly conserved amino-acid (rs7952293) | A = 0.245/ 536 |
|  | OR51Q1 | 11p | a nonsynonymous SNP rs2647574 (AA change=R/*) | T = 0.442/ 966 |
|  | OR51F1 | 11p | a polymorphism of C -> del at position 274 | - = 0.227/ 496 |
|  | OR51J1 | 11P | a nonsynonymous SNP in a highly conserved amino-acid (rs1909261) | A = 0.159/ 347 |
| 52 | OR52H1 | 11p | a nonsynonymous SNP in a highly conserved amino-acid (rs1586275) | T = 0.133/ 291 |
|  | OR52R1 | 11p | a nonsynonymous SNP in a highly conserved amino-acid (rs7941731) | G = 0.312/ 682 |
|  | OR52N4 | 11p | a nonsynonymous SNP rs4910844 (AA change=R/*) | T = 0.215/ 469 |
|  | OR52B4 | 11p | a polymorphism of C-> del at position 119 (rs11310407 | - = 0.328/ 716 |

These 40 SPGs are distributed in most OR families with SNP frequency between 0.02% in OR2S2 and roughly 50% in OR1E3p. Olfactory receptor families 2, 5 and 8 with 15 ORs were the largest families considered in this study. Data about olfactory receptors with SPGs was obtained from the Human Olfactory Data Explorer (HORDE).

hCNV-OR candidates were chosen based on large-scale CNV-identifications. CNV which involves gains or losses of between several and hundreds of kilobases of genomic DNA were identified by different techniques.

The method of array-based comparative genomic hybridization (array CGH) was applied for the analysis of the genomes of 55 unrelated individuals. By use of large insert DNA fragments, the arrays distinguished every 1 Mb throughout the human genome. The genomic DNA from 39 unrelated healthy control individuals was compared with genomic DNA from 16 individuals from whom chromosomal imbalances had previously been characterized. The comparative analyses allowed detection of all expected CNVs. This project has contributed as the main source for genomic variation databases, e.g. Database Genomic Variants (DGVs) and Human Olfactory Data Explorer (HORDE). CopySeq, was applied for the analysis of the genomes of 150 unrelated individuals with different ancestries. 34 hCNV-OR candidates were performed in pairs with CNV-features which were identified in the above mentioned projects as reported in Table 2.

TABLE 2

ORs known as CNV

| OR family | Olfactory receptors | Chromosome | Number of CNVs | Gain/ Deletion | Reference |
|---|---|---|---|---|---|
| 1 | OE1N1 | 9q | 2/150 | Gain | Waszak et al. 2010 |
|   | OR1S2 | 11q | 1/150 | Gain | Waszak |
| 2 | OR2T10 | 1q | 48/150 | Deletion | Waszak |
|   | OR2G6 | 1q | 1/150 | Gain | Waszak |
|   | OR2G3 | 1q | 2 of 55 | Deletion | Iafrate et al. 2005 |
|   | OR2L13 | 1q | 1 of 55 | Deletion | Iafrate |
|   | OR2T6 | 1q | 1/150 | Gain | Waszak |
|   | OR2A5 | 7q | 1/150 | Deletion | Waszak |
|   | OR2V1 | 5q | 1/150 | Gain | Waszak |
| 4 | OR4C11 | 11q | 58/150 | Deletion | Waszak |
|   | OR4K14 | 14q | 1/55 | Deletion | Iafrate |
|   | OR4P4 | 11q | 60/150 | Deletion | Waszak |
|   | OR4S2 | 11q | 61/150 | Deletion | Waszak |
|   | OR4C6 | 11q | 19/150 | Deletion | Waszak |
|   | OR4A47 | 11p | 2/150 | Deletion | Waszak |
|   | OR4C5 | 11p | 149/150 | Gain | Waszak |
|   | OR4F15 | 15q | 1/150 | Gain | Waszak |
|   | OR4F21 | 8P | 1/55 | Deletion | Iafrate |
|   | OR4K1 | 14q | 71/150 | Gain | Waszak |
|   | OR4K2 | 14q | 82/150 | Gain | Waszak |
|   | OR4K5 | 14q | 75/150 | Gain | Waszak |
|   | OR4C3 | 11q | 145/150 | Gain | Waszak |
|   | OR4M2 | 15q | 79/150 | Gain | Waszak |
|   | OR4N2 | 14q | 50/150 | Gain | Waszak |
| 5 | OR5AS1 | 11q | 1/150 | Deletion | Waszak |
|   | OR5L1 | 11q | 1/150 | Deletion | Waszak |
|   | OR5M9 | 11q | 2/55 | Deletion | Iafrate |
|   | OR5I1 | 11q | 1/150 | Deletion | Waszak |
| 6 | OR6C1 | 12q | 1/150 | Gain | Waszak |
| 10 | OR10AG1 | 11q | 2/55 | Deletion | Iafrate |
|   | OR10Q1 | 11q | 1/150 | Gain | Waszak |
| 51 | OR51A4 | 11q | 2/55 | Deletion | Iafrate |
| 52 | OR52E8 | 11p15 | 16/150 | Deletion | Waszak |
|   | OR52N5 | 11p15 | 42/150 | Deletion | Waszak |

These ORs were selected from two groups of variations in CNV as those that gain or loss of the genes. In addition, ORs as CNV were selected by their different distribution in the human population from 0.01% in OR1S2 to 99% in OR4C5. Most of these olfactory receptors were located in family 4.

B2. Large Scale Investigation of Olfactory Receptors

Figure 3:
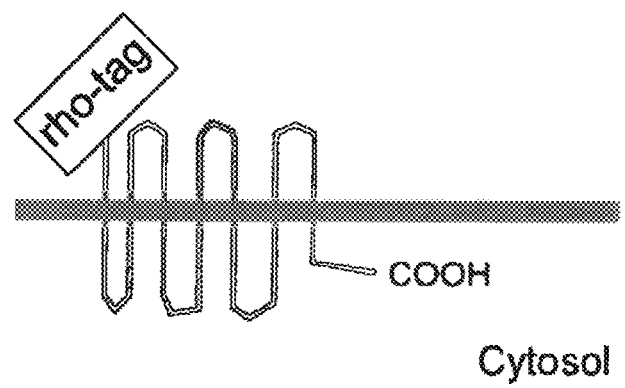
FIG. 3 illustrates Rhodopsin-tag.

To better understand the interaction between olfactory receptors with chemical odorants and the role of genetic variations in the phenotype of smelling, we analyzed the responses of 40 SPGs and 34 CNVs to 66 odorants with different chemical structures and different perceptions in humans. Libraries of human ORs were generated by the cloning of ORs in pCI plasmid as an expression vector that represents a large fraction of the SPGs and CNVs in human OR families (Tables 1 and 2).

pCI plasmids containing Rho-tag were used for cloning. The inclusion of the first 20 amino acids of rhodopsin (Rho-tag) at the N-terminal end has been shown to promote the cell-surface expression of some ORs. FIG. 3 shows the inclusion of the first 20 amino acids of rhodopsin at the N-terminal ends of OR has been shown to promote the cell-surface expression of ORs. PCRs were all done as described above and cloned in pCI vector supplemented with Rho-tag. After the cloning procedure all extracted plasmids were sequenced and those that were identified as pseudogene were excluded from the experiments.

To screen all of the 74 ORs with 66 odorants, due to the large number of ORs and odorants it was not possible to check all of them with the 66 odorants one by one. So we categorized chemical components into 7 different groups and then we selected those ORs that were activated by pools of odors.

To analyze the responses of ORs to the odorants, Ca-imaging was used. As described in section 2.5, calcium imaging of the transfected HEK293 cells was done by the use of columns an inverted microscope (Olympus; IX70) using a 10× objective (CPlanFL N Olympus). In experiments, Fura-2 Acetoxymethylester (Fura-2/AM) was used. Regardless of the presence of calcium, Fura-2 emits at the wavelength of 510 nm. Once Fura-2 had bound to free intracellular Ca2+ in cell plasma, the excitation wavelengths alternated between 340 and 380 nm and correlated to the amount of intracellular $Ca^{2+}$. According to this feature, the analysis of the 340/380 nm excitation ratio for Fura-2 allows us to quantify intracellular calcium levels.

Figure 4:
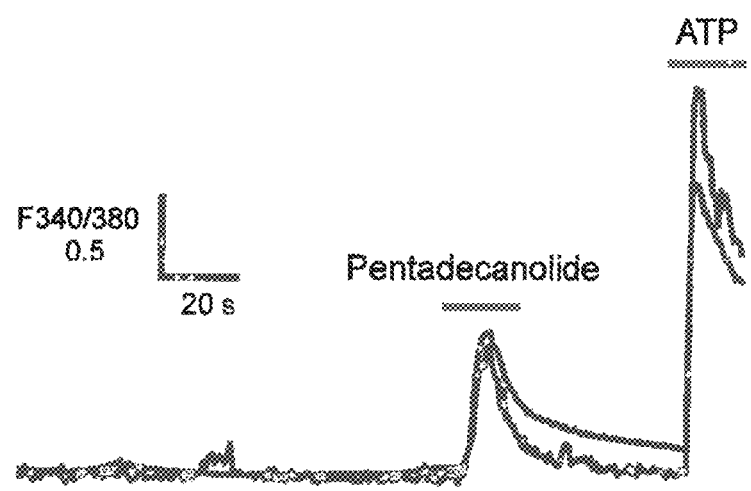
FIG. 4 is a graph illustrating Ca-imaging measuring, OR10Q1-transfected HEK293 cells responses to pentadecalactone.

In FIG. 4 transfected HEK293 cells with OR10Q1 are shown as an example, during screening with pentadecalactone. With increasing Ca2+ concentration fluorescence intensity is changed. In this case when the cells are stimulated with pentadecalactone, Ca-concentration will increase in the cells. The increasing of Ca-concentration was recorded as color changing by Cell-R software. Different levels of Ca-concentration are distinguished by color from dark blue (basic level of internal Ca-concentration) to red (highest level of Ca-concentration) by the cell-R software. At the end of the measurements, cells responded to ATP (as a marker of cell vitality) strongly with an increase of internal $Ca^{2+}$.

As a first step, transfected HEK293 cells with ORs were monitored for increases in intracellular calcium during sequential measuring with the 7 odorant mixtures containing 100 μM of each odorant. Of the 74 ORs tested, 38 responded to one or more mixtures and were suitable for analysis; the other 36 ORs were excluded from further analysis (FIG. 14).

B3. Deorphanization of Olfactory Receptors

Out of the 74 olfactory receptors, 38 of the ORs (51.3%) showed a response to at least one mixture at 200 μM concentration. We then applied the 66 odorants individually at 200 μM to the mixture-responsive ORs. Following the strategy for deorphanization, at the end of the procedure 18 human ORs (24%) showed a significant response (p<0.05) to at least one of the 66 odorants related to specific anosmia. Positive response was determined by the timing of the response, the strength of the response (more than twofold higher than the noise amplitude of the baseline), and the shape of the response curve (sharp rise in curve with gradual recovery). 20 receptors did not show any significant results, and were excluded from the next step of experiments.

Hek293 cells transfected with OR1B1, OR2L8, OR4X2, OR8D2, OR8B4 and OR10AQ1. It was observed that these ORs responded to ketone, amber, ketone, alcohol, aldehyde and musk odorant groups respectively. According to the strategy for deorphanization, all of the olfactory receptors responding to odorant groups were screened with odorants in subgroups. After the final step of deorphanization it was observed that OR1B1 was significantly (P<0.05) activated by Calone, androstenone and 3-hydroxy-2-methyl-4-pyranone which all belongs to the ketone group. However, although OR1B1 responded to other groups of odorants further investigation did not show any significant activation of this receptor by single substances of other mixtures. The same strategy was used for the screening of OR2L8 with the amber group as a unique group that activated OR2L8.

Ca-imaging results showed that the Ca2+ concentration increased in transfected cells with OR2L8 during the screening of the cells with Timbrol and Yasamber as individual odorants in the amber group. Also, OR4X2 responded to ketone group. In the following screening procedure by Ca-imaging, it was found that OR4X2 could be the receptor for 2-aminoacetophenon (P<0.05). OR8D2, as a further deorphanized olfactory receptor, responded during group screening to the amber and alcohol groups, but during the subgroup screening only two odorants of the alcohol group, Muguet alcohol and alcohol C6, significantly activated OR8D2 (P<0.05). No reaction was observed when individual odorants of the amber group were applied to this receptor (P>0.05). OR8B4 responded significantly to Anisic aldehyde and aldehyde C6 as two odorants of the aldehyde group (P<0.05). 12 ORs were activated by the musk odorant mixture. However, only three of them responded to individual musk odorants in the screening of single substances. One of these was OR10Q1 which significantly responded to Cyclopentadecanolide (P<0.05). In addition to the musk group, OR10Q1 also responded to the amber group mix but the application of single amber odorants did not produce any response.

Ca-imaging graphs of responding ORs including OR1B1, OR2L8, OR4X2, OR8D2, OR8B4 and OR10Q1 which, as mentioned above, are shown in detail in Table 4 and FIG. 5.

TABLE 4

Cell responses

| | | | Number of cell responses | |
|---|---|---|---|---|
| Ex. | OR | Odorant | Control | Experiment |
| 1 | OR1B1 | 3-Hydroxy-2-methyl-4-pyranone | 5 | 35 |
| | | Calone | 0 | 9 |
| | | Andorestenone | 0 | 20 |
| 2 | OR2L8 | Yasamber K | 2 | 10 |
| | | Timberol | 1 | 10 |
| 3 | OR4X2 | Hexanal | 0 | 8 |
| | | Anisic aldehyde | 0 | 14 |
| 4 | OR8D2 | Octanol | 0 | 9 |
| | | Muguet Alcohol | 0 | 21 |
| 5 | OR10Q1 | Pentadecanolide | 2 | 52 |

Figure 5A:
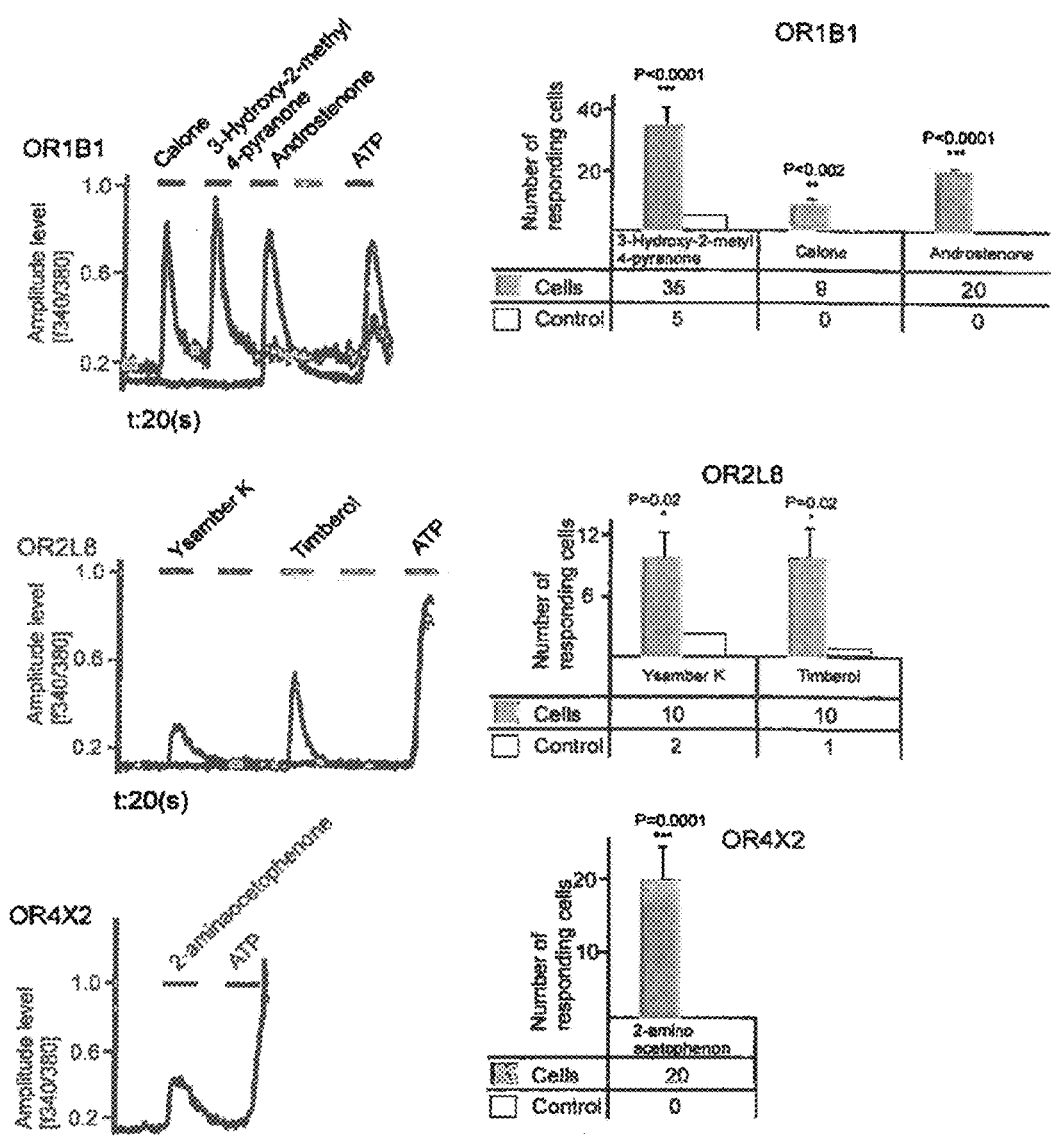
FIGS. 5A and 5B each illustrate graphs showing significant responses of olfactory receptors to individual odorants related to specific anosmia.
Figure 5B:
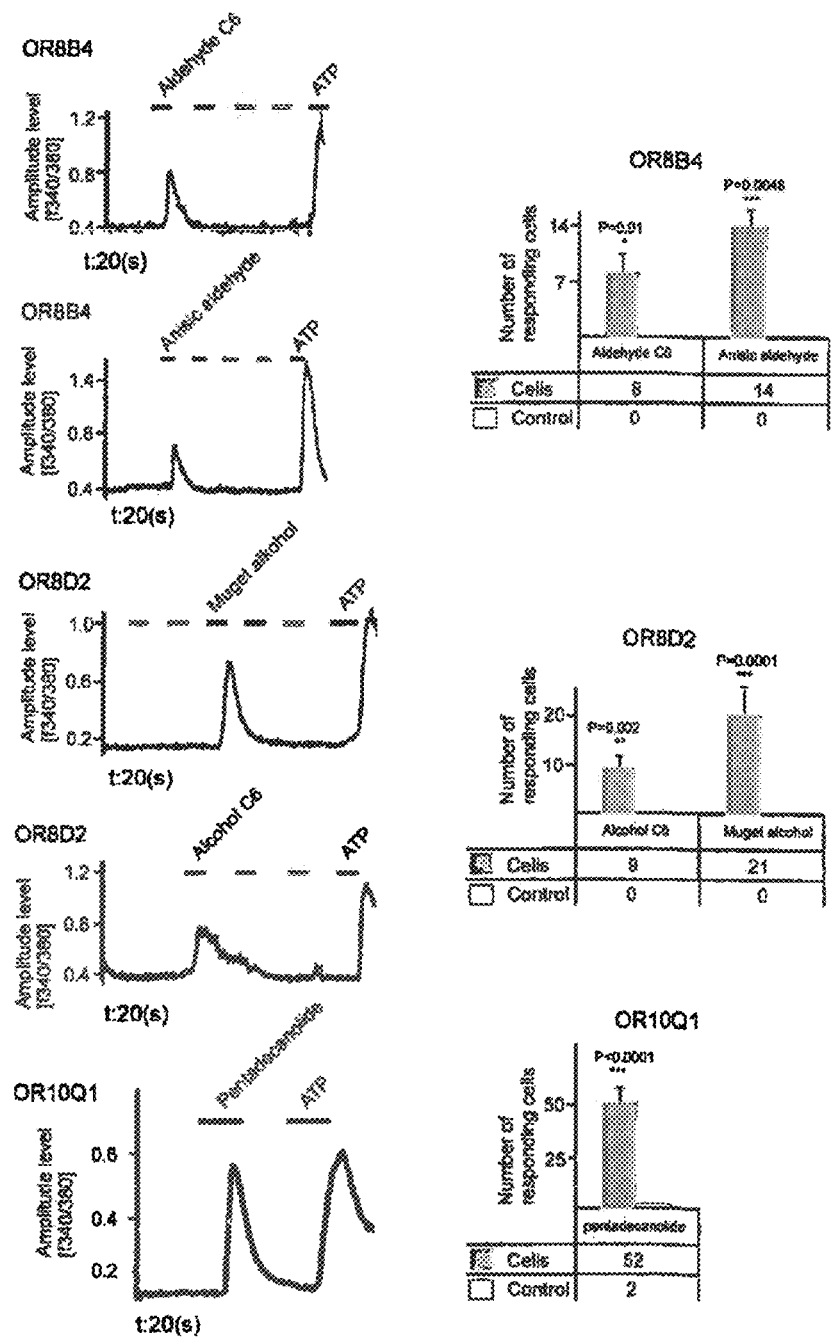

Every curve in line charts of FIG. 5 represents intracellular calcium increases of a single cell by the stimulation of a particular individual odorant with concentration of 200 μM. In line charts, cells responded at the end also to ATP, which evidenced for cell viability. To find out if the individual odorants significantly activated the receptor, we counted all responded cells at final stage of three times measuring and tested for significance by using Chi-square test (Column chart). P-value was calculated by number of transfected cells (approximately 2000 transfected cells in three times of measuring) vs. number of cell responses in two groups (in test samples and control samples). Bars indicate the SEM (p*<0.05, 0.001<P<0.0001 and P*<0.0001 according to Chi-square test). First diagram shows responses of OR1B1 to Calone, androstenone and 3-hydroxy-2-methyl-4-pyrane. Expressed OR1B1 induced totally 20, 35, 9 cell responses to Calone, androstenone and 3-hydroxy-2-methyl-4-pyrane respectively (column chart) in comparison to 0, 0, 5 cells response in controls; p-value <0.05 (2000 cells were screened during three times of measuring). Line chart show responses curves in one measurement. Second diagram shows responses of OR2L8 to Timbrol and Yasamber. Expressed OR2L8 induced totally 10 cell responses to both of odorants (column chart); p-value <0.05 evaluated significant response. Line chart show responses curves in one measurement. Third diagram shows responses of OR4X2 to 2-aminoacetophenone. Expressed OR4X2 induced totally 20 cell responses to 2-aminoacetophenone (column chart) in comparison with cell response in controls; p-value <0.05 (2000 cells were screened during three times of measuring). Line chart show responses curves in one measurement. Next diagram is responses of OR8B4 to Anisic aldehyde and aldehyde C6. Expressed OR8B4 induced totally 14 and 8 cell responses to Anisic aldehyde and aldehyde C6 respectively (column chart); p-value <0.05 evaluated significant response. Line chart show responses curves in one measurement. OR8D2 responded to Muguet alcohol and alcohol C6. Expressed OR8D2 induced totally 9 and 21 cell responses to alcohol C6 and Muguet alcohol respectively (column chart); p-value <0.05 evaluated significant response. Line chart show responses curves in one measurement. Las diagram shows responses of OR10Q1 to Pentadecalactone. Expressed OR10Q1 induced totally 52 cell responses to Pentadecalactone (column chart) in comparison with 2 cells response in controls; p-value <0.05 evaluated significant response (2000 cells were screened during three times of measuring). Line chart show responses curves in one measurement. Control HEK293 cells were transfected with all cofactors and pCI plasmids without ORs.

Among the total 18 deorphanized receptors 6 receptors belong to the CNV group and 12 ORs are known as SPG as shown in Table 5. Despite the other receptors not producing a significant response to single odorants from one or more odorant mixtures, our positive responses resulted in the discovery of a large number of OR agonists. The first 12 OR represent SPGs, the remaining 6 CNVs; CAN stands for the carbon number.

TABLE 5

18 olfactory receptors responded to 32 odorants in related with specific anosmia

| Groups | Odorant | CAN | OR1B1 | OR2L8 | OR4X2 | OR4C16 | OR5L1 | OR8B4 | OR8D2 | OR10A6 | OR10C1 | OR12D2 | OR52B4 | OR4E2 | OR4P4 | OR4K2 | OR4K5 | OR4C3 | OR5I1 | OR10O1 |
|---|---|---|---|---|---|---|---|---|---|---|---|---|---|---|---|---|---|---|---|---|
| Ketone | 3-Hydroxy-2-Methyl-4-Pyran | 6 | ■ | | | | | | | | | | | | | | | | | |
| Ketone | calone | 10 | ■ | | | | | | | | | | | | | | | | | |
| Ketone | Androstenon | 19 | ■ | | | | | | | | | | | | | | | | | |
| Amber | Yasamber K | 17 | | ■ | | | | | | | | | | | | | | | | |
| Amber | Timbrol | 15 | | ■ | | | | | | | | | | | | | | | | |
| Ketone | 2-aminoacetophenon | 8 | | | ■ | | | | | | | | | | | | | | | |
| Lactone | Aldehyde C18 | 9 | | | | ■ | | | | | | | | | | | | | | |
| Ketone | B-Damascone | 13 | | | | ■ | | | | | | | | | | | | ■ | | |
| Aldehyde | Anisic aldehyde | 8 | | | | | ■ | | | | | | | | | | | | | |
| Aldehyde | Aldehyde C6 | 6 | | | | | ■ | | | | | | | | | | | | | |
| Alcohol | Alcohol C6 | 6 | | | | | | ■ | | | | | | | | | | | | |
| Alcohol | Muguet alcohol | 11 | | | | | | | | ■ | | | | | | | | | | |
| Alcohol | Cinamyl alcohol | 9 | | | | | | | | ■ | | | | | | | | | | |
| Ketone | Hedione | 13 | | | | | | | | ■ | | | | | | | | | | |
| Ketone | 2-butanone | 4 | | | | | | | | | ■ | | | | | | | | | |
| Acid | Acetic acid | 2 | | | | | | | | | | ■ | | | | | | | | |
| Acid | Isovaleric acid | 5 | | | | | | | | | | ■ | | | | | | | | |
| Acid | Propionic acid | 3 | | | | | | | | | | ■ | | | | | | | | |
| Ketone | 1-Octan-3-One | 8 | | | | | | | | | | | ■ | | | | | | | |
| Mix | 2-4-6 trichoroanisole | 11 | | | | | | | | | | | ■ | | | | | | | |
| Mix | Sandranol | 14 | | | | | | | | | | | | ■ | | | | | | |
| Mix | Geosmin | 12 | | | | | | | | | | | | ■ | | | | | | |
| Acid | N-Hexanoic acid | 6 | | | | | | | | | | | | | ■ | | | | | |
| Musk | Globalide | 15 | | | | | | | | | | | | | ■ | | | | | |
| Aldehyde | Banzaldehyde | 7 | | | | | | | | | | | | | | ■ | | | | |
| Aldehyde | 3-phenyl propyl aldehyde | 9 | | | | | | | | | | | | ■ | | ■ | | | | |
| Aldehyde | Isobutyr aldehyde | 4 | | | | | | | | | | | | | | | ■ | | | |
| Amber | Cedramber | 16 | | | | | | | | | | | | | | | | ■ | | |
| Acid | Isocaproic acid | 6 | | | | | | | | | | | | | | ■ | | | | |
| Aldehyde | Octanal | 8 | | | | | | | | | | | | | | | | | ■ | |
| Alcohol | Graniol | 10 | | | | | | | | | | | | | | | | | ■ | |
| Musk | Pentadecanolide | 15 | | | | | | | | | | | | | | | | | | ■ |

The failure of a specific OR to respond to any of the tested odorants may reflect a failure of the OR to expression in our assay method rather than a lack of sensitivity to the tested odorants. In our further analysis we only selected receptors that responded to at least one of the tested odorants, and were therefore rated functional in our assay.

Each odorant mixture stimulated a subset of olfactory receptors and some mixtures activated more receptors than others. Noticeably, 33% (6/18) of the ORs were activated by mixtures containing ketones, 22% (4/18) with aldehydes and 16% (3/18) of the ORs responded to the alcohols and musk groups, whereas only 11% (2/18) of receptors responded to the amber and "mix" groups. Regarding the number of odorants per mixture, 8 ketones and 6 aldehydes activated 5 SPGs and 1 CNV and 2 SPGs and 2 CNV receptors respectively, while just 3 odorants from the mix group activated only 2 SPGs receptors and 2 odorants from the musk group activated 3 CNVs receptors. 22% (9/40) and 17% (7/40) responded to ketone and aldehyde odorants. 10% (4/40) of responses were evoked by the amber and mix groups. Carboxylic acids and alcohols constitute 15% (6/40) of all activating odorants. Only 7% (3/40) of the responses were induced by the musk group.

B4. Ca-Imaging and CRE-Luciferase: Similarities and Differences

Figure 6:
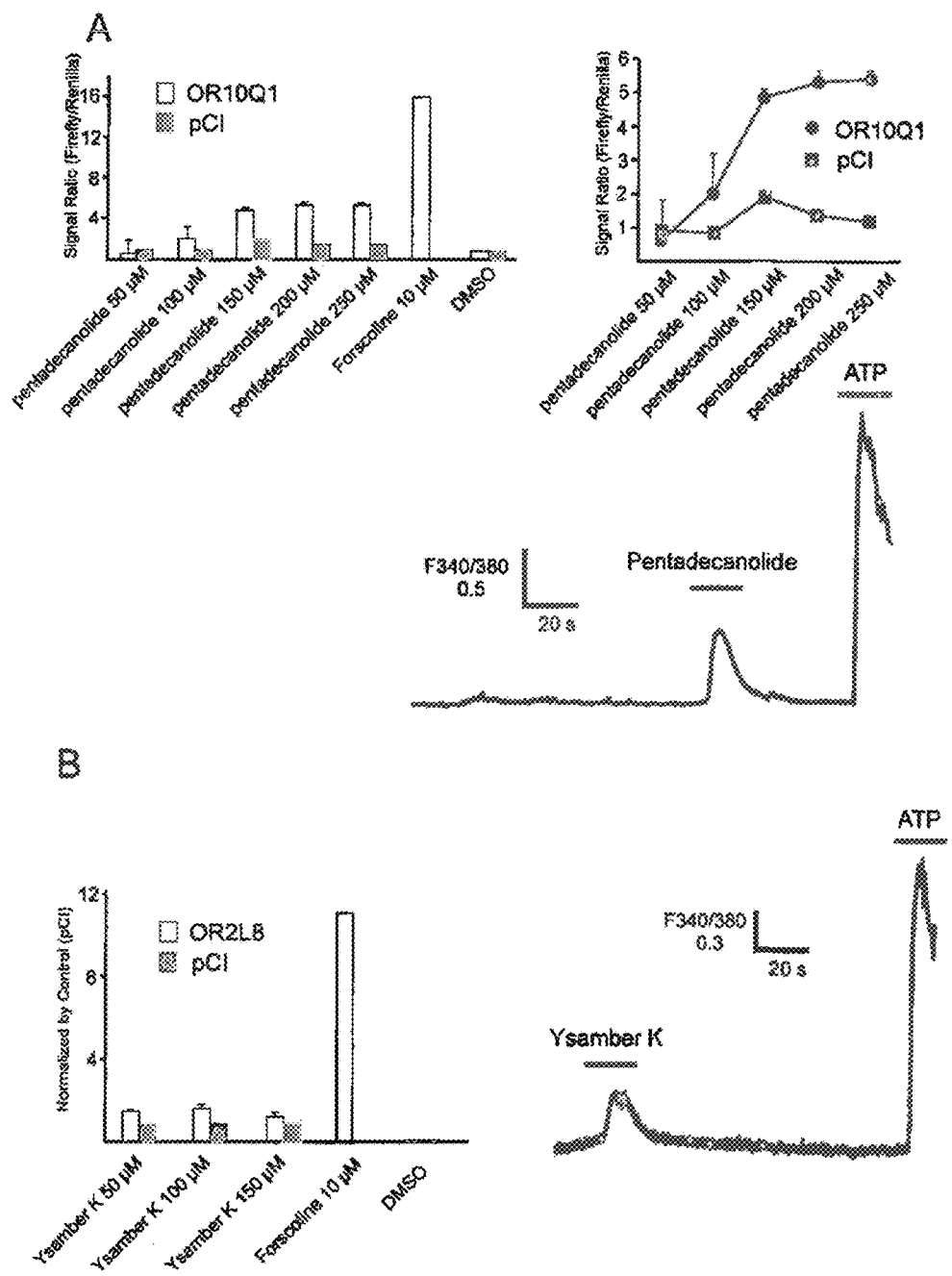
FIG. 6 illustrates graphs showing activation of OR10Q1 and OR2L8 by Ca-imaging and CRE-Luciferase.

Despite numerous studies on olfactory receptors, many vertebrate ORs are still orphan. One reason could be that the recombinant expression system requires additional components that allow for the expression of enough OR protein in the cell membrane. In addition, it is supposed that for odorants to stimulate cellular pathways they need cofactors to associate with the cAMP pathway (therefore, assays like CRE-luciferase have been developed). We tried to confirm the Ca-imaging results by a CRE-luciferase assay. By Ca-imaging, 6 ORs (OR1B1, OR2L8, OR4X2, OR8B4, OR8D2 and OR10Q1) were deorphanized as receptors for particular odorants. Similar experiments for these 6 ORs were carried out by the CREluciferase assay and all were stimulated with their ligands identified by Ca-imaging results. Experiments with the CRE-luciferase assay showed a difference in ligand-responsiveness as measured by $G\alpha15$-mediated Ca-imaging and $G\alpha s$-mediated cAMP elevation. OR1B1, OR4X2, OR8D2 and OR8B4 deorphanized by Ca-imaging but did not produce similar responses by CRE-luciferase assay. OR10Q1 gave positive responses in the Ca2+ assay and also gave positive responses in the cAMP assay and OR2L8 produced a weak answer by the cAMP assay as shown in FIG. 6:

(A) Column and line charts show dose curve of OR10Q1 in responding to pentadecalactone in concentrations of 50 μM, 100 μM, 150 μM, 200 μM and 250 μM. pCI vector transfected cells and DMSO (0.2%) used as negative controls and Forskolin (Fr) used as a positive control with 10 μM concentration. CRE-Luciferase results were reported as ratio of firefly to renila. Line chart in middle show responses of OR10Q1 to pentadecalactone by Ca-imaging.

(B) Column chart shows weak response of OR2L8 for Yasamber in concentration of 50 μM, 100 μM and 150 μM. DMSO used as negative control and Forskolin (Fr) used as a positive control with 10 μM concentration. CRE-Luciferase results were reported according to normalization of receptor responses to DMSO as control. Line chart in right shows responses of OR2L8 to Yasamber by Ca-imaging.

B5. Cell Surface Expression of Olfactory Receptors

Measuring the activation of ORs upon odorant stimulation is important for studying odorcoding by the ORs. One critical step after expression of OR proteins is trafficking of proteins to the plasma membrane. For evaluating the cell-surface expression and measuring the functional activation of ORs, cofactors plasmids including RTP1, Myr-Ric8A, HSC70 and $G\alpha15$ were expressed in HEK293 cells transiently. With the use of fluorescent immunocytochemistry in live cells, we measured cell surface expression level of ORs.

B6. Broadly-Narrowly Tune of Olfactory Receptors

In olfaction research, due to the lack of an agreed metric scale for measuring odorant similarity, there is no quantitative scale to rate receptors as broadly or narrowly tuned but traditionally it has been measured in terms of a receptor's number of agonists and also the similarity of those agonists to each other. According to current study, of 18 SPGs and CNVs activated by mixtures, 66.6% (12 of 18) responded to only one mixture containing structurally related odorants. In subgroups, 4 of the 18 deorphanized receptors (22.2%) responded to only one odorant and the other 66.7% (12 of 18) responded to up to three odorants, whereas only 2 of 18 (11.1%) responded to more than 3 odorants and none responded to all odorants in the mixture. In most cases, the odorants recognized by olfactory receptors had related chemical functional groups. Some examples are OR1B1, which selectively responded to three odorants from the ketone mixture, including 3-hydroxy-2methyl-4pyran, Calone and androstenone. OR8D2 responded to alcohol C6 and Muguet alcohol, and two odorants from the alcohol mixture or OR2L8 responded to Yasamber and Timbrol, two odorants from the amber group. In general we confirmed in this study that a single OR can recognize multiple odorants. Out of 18 ORs, 14 ORs responded to more than one odorant. Similar results are shown in other studies were single olfactory neuron or olfactory receptors in recombinant systems can respond to multiple odorants.

Our results show that some SPGs and CNVs are narrowly tuned to recognize a relatively low number of odorants that are categorized in a particular group according to chemical structure. In addition, the results show that there are some single odorants (8/32) that can be recognised by multiple receptors. Yasamber is detected by OR2L8 (from the SPG group) and OR4K5 (from the CNV group). Also, Muguet alcohol and alcohol C6 are detected by OR8D2 and OR10A6.

B7. Distance Between Odorants and Response Variability in the Olfactory System

To measure the distance between two odorants, we used different metrics by counting carbon atom numbers (CANs) and functional group. To estimate the response pattern in correlation with CAN, the odorants were restricted to vary only in CAN with all other features such as functional group fixed. With regard to CANs, we classified the deorphanized odorant into 9 groups. It can be seen that among these groups odorants with 8-9 atom carbon numbers constitute the largest group, with 9 responses. Odorants with low CANs (between 2 and 5) and high CANs (between 16 and 19) showed minimum responses to olfactory receptors. According to our results, 40% (16/40) of CANs of all the reactive odorants were between 6 and 9. The results are reflected in Table 6 showing that odorants with less than 5 or higher than 12 carbon atom numbers activated low numbers of ORs in comparison with odorants containing between 5 and 12 CANs.

TABLE 6

Correlation between number of deorphanized odorant and carbon atom numbers

| CAN | Number of deorphanized odorants |
|---|---|
| 2-3 | 2 |
| 4-5 | 3 |
| 6-7 | 7 |
| 8-9 | 9 |
| 10-11 | 6 |
| 12-13 | 4 |
| 14-15 | 5 |
| 16-17 | 3 |
| 18-19 | 1 |

Also, to find a discernible structural feature that might be recognized by the OR, we considered structural features of multiple odorants that are recognized just by one single OR. As can be seen in Table 5, some of the receptors responded to odorants with a close number of carbon atoms. For example, OR2L8 or OR4K5 responded to odorants with between 15 and 17 CANs and OR4E2 showed some signal with odorants with between 9 and 11 CANs and OR8B4 between 6 and 8. No responsive receptors recognized odorants of all the lengths tested (i.e. C2-C19); these results were consistent with previous observations. However, it should also be noted that there are ORs responding to odorants with greatly different CANs. For example, OR1B1 responded to 3-hydroxy-2mytyl-4pyran with 6 CANs and also responded to androstenone with 19 CANs.

The other factor that could be observed as a connection between olfactory receptors and odorants are chemical functional groups. The functional groups of the odorants as reported in previous studies are also important in recognition of ORs. In the experiments none of the ORs recognized odorants belonging to all five groups (alcohols, acids, ketones, aldehydes, ambers) of test odorants and 61.1% (11/18) of ORs recognized odorants of only one class. Ketones constitute most parts of this odorant class with 6 subgroups and the other groups including acid, amber, aldehyde and alcohol responded with the same number of 3 odorants. The following Table 7 refers to ORs responded to odorants with similar functional groups.

TABLE 7

OR and Odorants with similar functional groups

OR12D2
Acetic Acid
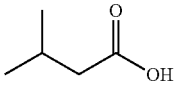
Isovaleric acid
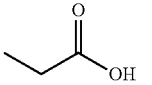
Propanoic acid OR1B1
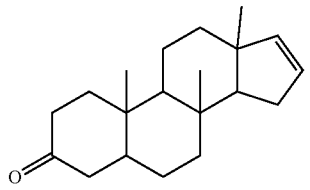
5α-Androst-16-en-3-one
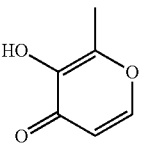
3-Hydroxy-2-methyl-4-pyrone
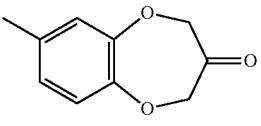
Calone OR8B4
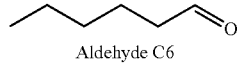
Aldehyde C6
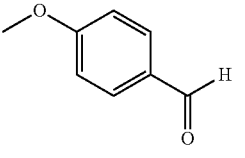
Anisic aldehyde OR8D2
Alkohol C6
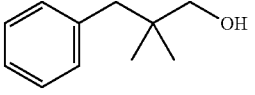
Muguetalkohol OR10A6
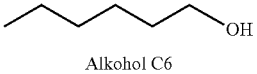
Alkohol C6
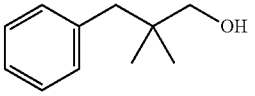
Muguetalkohol
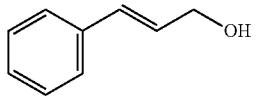
Cinnamic alcohol

TABLE 7-continued

OR and Odorants with similar functional groups

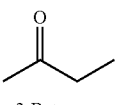

OR10C1     2-Butanone     Hedione

The remaining ORs recognized odorants that belonged to two or three chemical classes. This diversity in the recognition properties of ORs is likely to be of central importance to the olfactory system's ability to detect and discriminate a wide variety of structurally diverse odorants.

B8. Similar Odorant Structure, Similar Response?

Figure 7:
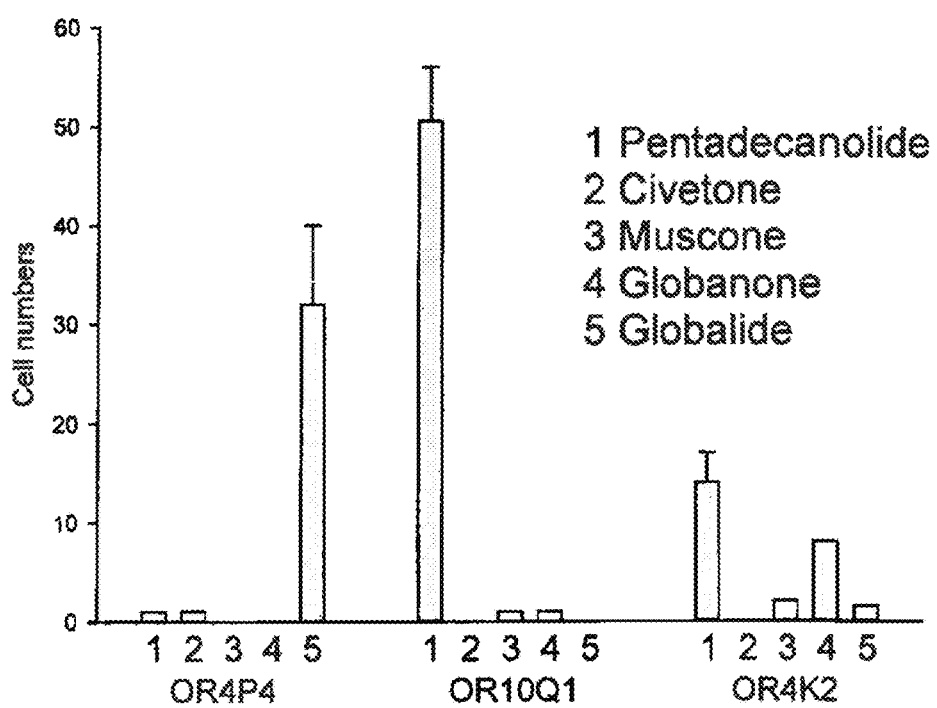
FIG. 7 is a graph showing musks with similar chemical structures do not produce the same responses.

As shown in Table 7, most of the ORs responded to odorants with similar functional groups but not with similar chemical structures. To understand the relation between structure similarity and similar response pattern, we selected OR10Q1, OR4K2, OR4P4 and OR1B1. According to our data file, OR10Q1 and OR4K2 responded to Pentadecanolide and OR4P4 and OR1B1 responded to Globalide and androstenone respectively. OR10Q1, OR4K2 and OR4P4 were measured with other musk odorants (Pentadecanolide, Civetone, Muscone, Globanone and Globalide) with a similar base of chemical structures. But ORs which responded to musk odorants did not show any significant responses to other musk odorants with similar chemical structures as set out in FIG. 7.

For example, Civetone is closely related to muscone, the principal fragrant compound found in musk, because both compounds are macrocyclic ketones. Pentadecanolide and globalide are known as lactone musks, and muscone, civetone and globanone are in the ketone musk group. Structurally related odorants were individually tested in vitro by Ca-imaging for their ability to activate OR4P4, OR10Q1 and OR4K2. The column chart shows the number of cells that responded to different musks during measuring by Ca-imaging. Approximately 2000 cells were screened during three times of measuring.

As shown before, OR1B1 is a deorphanized receptor for androstenone. To understand the relation between structure similarity and similarity in response pattern, we screened OR1B1 with testosterone as a chemical substance with close structural similarity to androstenone. Ca-imaging results showed that OR1B1 responded to testosterone as well as to androstenone. Testosterone is a steroid hormone from the androgen group and is found in mammals. It is the principal male sex hormone and an anabolic steroid.

Figure 8:
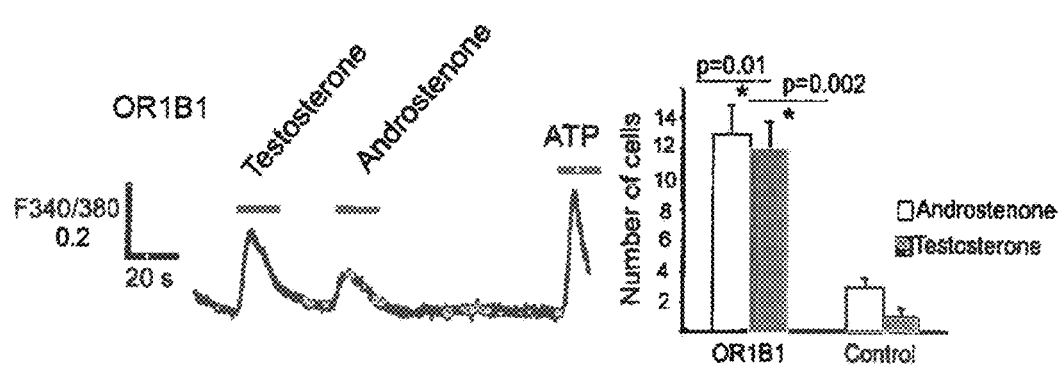
FIG. 8 is a graph also showing musks with similar chemical structures do not produce the same responses.

FIG. 8 refers to steroid hormones with similar chemical structure produced similar responses by Ca-imaging technique. OR1B1 responds to androstenone and testosterone (200 μM). In this study it was shown OR1B1 also responded to Calone and 3-hydroxy-2-methyl-4-pyrane (200 μM). In the second approach to compare responses between similar chemical structures testosterone was used as an androgen with a similar chemical structure to testosterone. OR1B1 induced in total 13 and 12 cell responses for androstenone and testosterone respectively (column chart) in comparison with 3 and 1 cell response in controls, p-value <0.05, evaluated a significant response. Control HEK293 cells were transfected with all cofactors and pCI plasmids without ORs. The line chart shows response curves in one measurement of androstenone and testosterone. Approximately 2000 cells were screened during three times of measuring.

B9. Relation Between Odor Specificity and Receptor Sequence

Figure 9A:
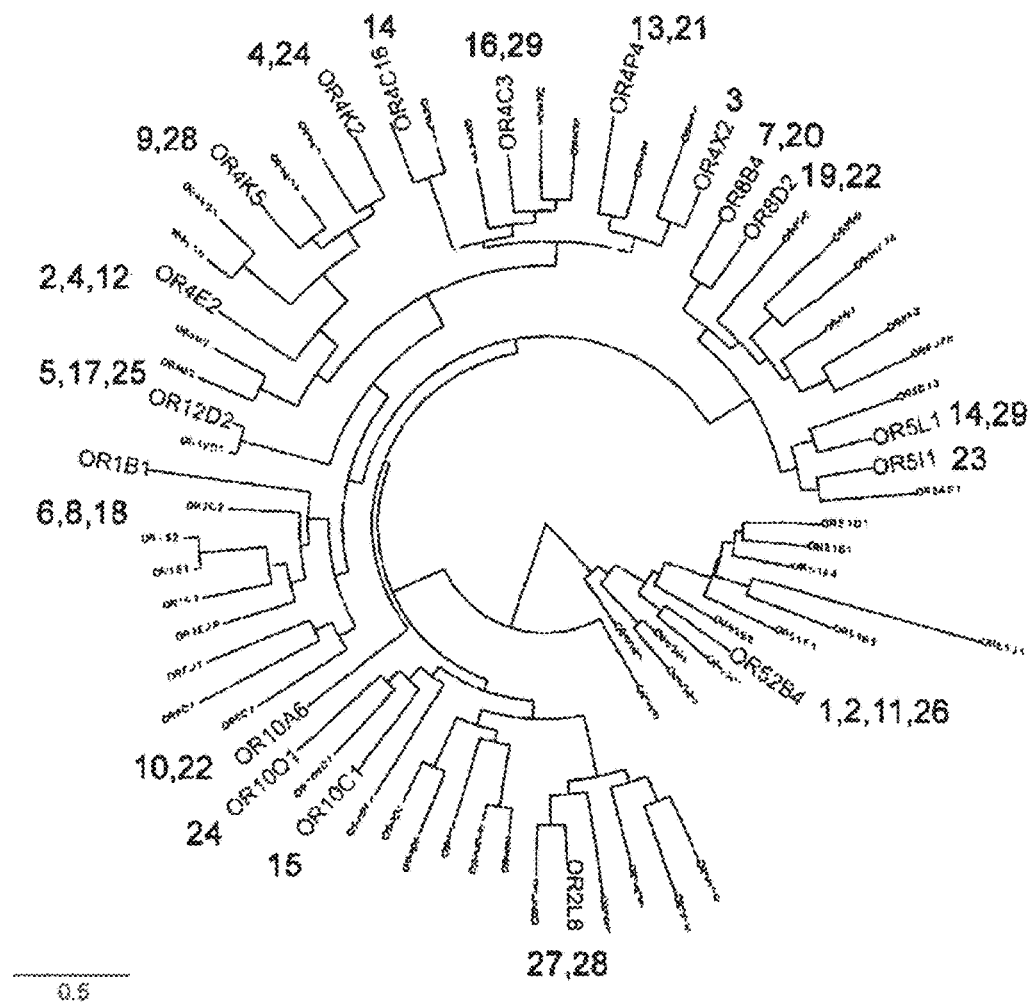

Using the similarity of amino acid properties, a dendrogram of 74 ORs were constructed which were screened in this study to show the distribution of ORs with known ligands among OR classes and families. The dendrogram is depicted in FIG. 9.

Figure 10:
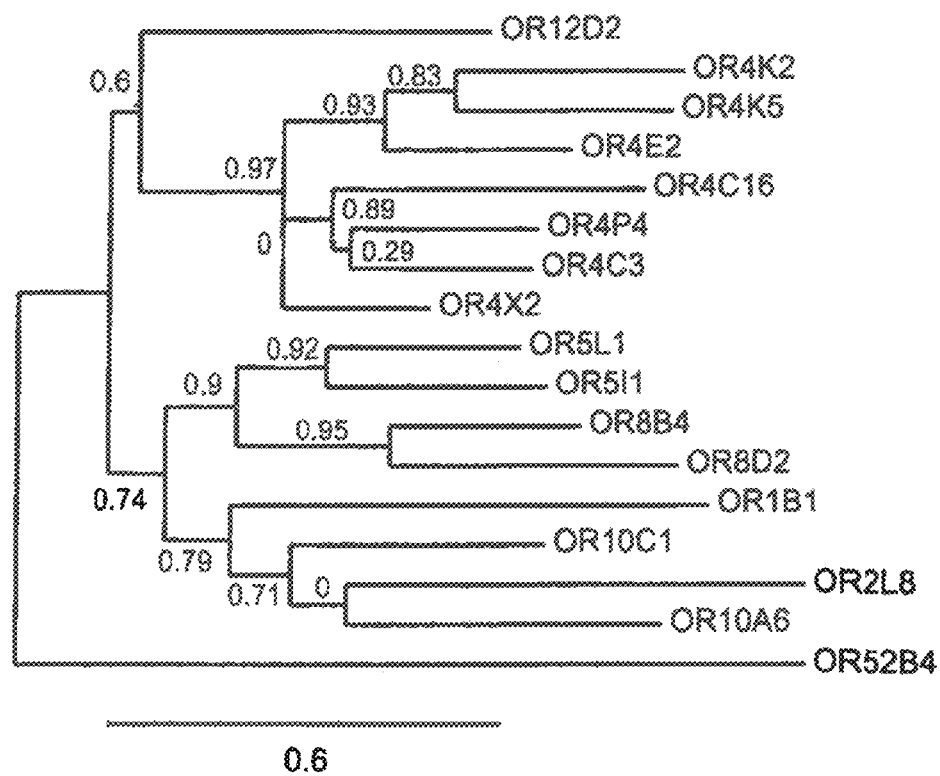
FIG. 10 illustrates a phylogenic tree of 74 olfactory receptors which are known as SPGs or Dendrogram of TM3-TM6 as a particularly variable region in deorphanized odorant receptors.

For the purpose of the present invention a considerable number of ORs were deorphanized and, next, odor specificity and sequence of the ORs were matched. One common hypothesis is that ORs that are activated by the same odorant will have similar protein sequences or amino acids in a potential binding pocket. To test this hypothesis a dendrogram based on the protein sequence of the TM3-TM6 region was constructed, a particularly variable region in ORs that has also previously been proposed to be involved in OR-odorant interactions. In this dendrogram (FIG. 10), a map of the newly identified ligands is presented. The dendrogram compares the TM3-TM6 regions of 18 ORs that responded with 32 odorants. For some of our new ligands, it was found that the same odor activates closely related receptors from the same Glade but for others, receptors from different clades are activated. For example, OR4P4 and OR4C3 are in the same Glade and are activated by acids. It seems these sequences do not necessarily correspond to the binding site of the ORs. It was found that TM3-TM6 sequence identities among the 18 ORs that recognized odorants in relation to specific anosmia. Red numbers are branch support values as a likelihood ratio based on the confidence that these branches are neighbors. Variable regions of the ORs were compared with using the Phylogeny.fr online program.

B10. Single Nucleotide Polymorphism and Odorant Responses: Functional Analysis of OR1B1 and OR10Q1-Mutants Human olfactory perception differs enormously between individuals, with large reported perceptual variations in the intensity and pleasantness of a given odor. Androstenone (5α-androst-16-en-3-one), an odorous steroid derived from testosterone, is variously perceived by different individuals as offensive ("sweaty, urinous"), pleasant ("sweet, floral") or odorless. The mechanistic basis of variation in odor perception between individuals is unknown. As it has previously been shown that androstenone perception is dependent on genetic variation in human odorant receptor genes it was tried to investigate whether genetic variation in OR1B1 could be effective in odorant responses. Here we show that a human odorant receptor, OR1B1, is activated in vitro by androstenone and testosterone.

A search for polymorphisms in OR1B1 in SNP databases identified 3 non-synonymous SNPs in this receptor, occurring at frequencies greater than 25%. We refer to the most common allele of this receptor, named OR1B1-574, OR1B1-688 and OR1B1-789. Three different common variants of this receptor contain non-synonymous single nucleotide polymorphisms (with MAF>0.25), resulting in three amino acid substitutions that severely impair function in vitro. It was screened for androstenone and testosterone-mediated stimulation with Ca-imaging and generated odorant receptors with each of the SNPs and found that OR1B1-574 was not able to reproduce responses to androstenone and testosterone with a concentration of 200 µM.

Figure 11:
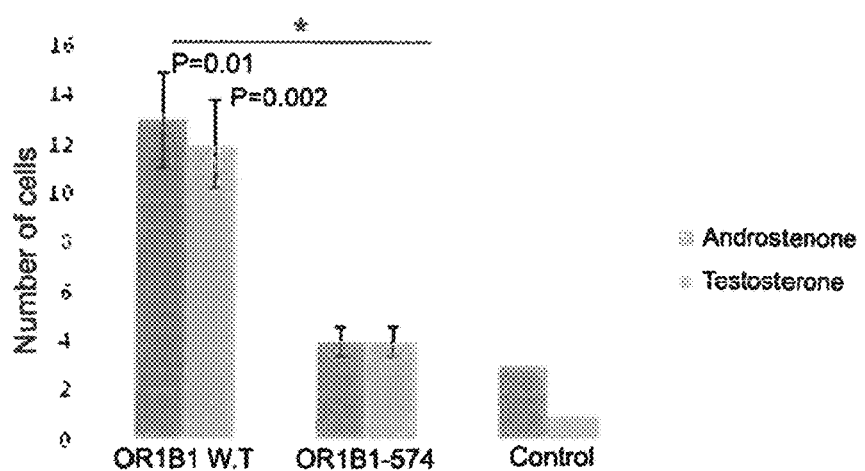
FIG. 11 illustrates a graph showing responsiveness of OR1B1-574 to androstenone and testosterone in comparison to OR1B1 WT as examined by Ca-imaging measurements on receptors heterologous expressed in HEK293 cells.

FIG. 11 shows the responsiveness of OR1B1-574 to androstenone and testosterone in comparison to OR1B1 WT as examined by Ca-imaging measurements on receptors heterologous expressed in HEK293 cells. Cell responses were quantified with unspecific activity of androstenone and testosterone in controls. HEK293 cells as controls were transfected with all cofactors and pCI plasmids without ORs. Both odorants were applied for 20 seconds with a concentration of 200 µM. Bars indicate the SEM (*p<0.05 according to Chi-square test). Control cells respond to androstenone and testosterone (3 and 1 cells respectively). Approximately 2000 cells were screened during three times of measuring.

OR1B1-688 and OR1B1-789 did not show any significant differences responses in comparison with OR1B1 WT.

Figure 12:
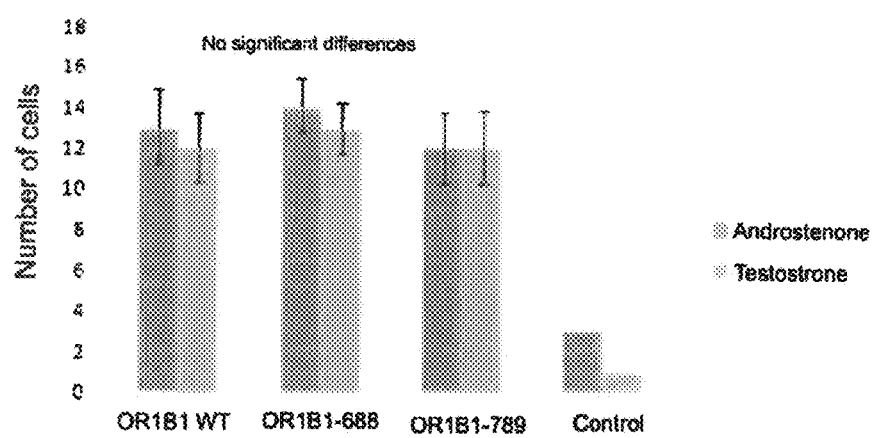
FIG. 12 illustrates a graph showing no significantly different responses of OR1B1-688 and OR1B1-789 to androstenone and testosterone in comparison to OR1B1 WT as examined by Ca-imaging measurements on receptors heterologous expressed in HEK293 cells.

As shown in FIG. 12 no significantly different responses of OR1B1-688 and OR1B1-789 to androstenone and testosterone in comparison to OR1B1 WT occurred as examined by Ca-imaging measurements on receptors heterologous expressed in HEK293 cells. Cell responses were quantified with unspecific activity of androstenone and testosterone on nontransfected cells with ORs as controls. Both odorants were applied for 20 seconds with a concentration of 200 µM. Bars indicate the SEM. Control cells respond to androstenone and testosterone (3 and 1 cells respectively).

Pentadecalactone is known as an odorant with a specific anosmia of 12% in humans. With the observation of the Mendelian inheritance pattern of pentadecalactone it is supposed that this specific anosmia is due to an inheritable defect in one of the olfactory receptor proteins.

Further on, it was investigated whether genetic variation in OR10Q1 as a new deorphanized receptor for pentadecanolide could be effective in odorant perception or not. A search for polymorphisms in OR10Q1 in SNP databases identified one non-synonymous SNP in this receptor, occurring at frequencies greater than 0.05%. We refer to the most common allele of this receptor, named OR10Q1-614. A common variant of this receptor contains non-synonymous single nucleotide polymorphisms (with MAF of 14.88%), resulting in amino acid with substitution of Cys instead of Arg. To estimate the role of this SNP, it was targeted for site directed mutagenesis by PCR driven overlap extension and cloning into an expression vector. Mutation of this frequent SNP was considered to affect responsiveness of the receptor to pentadecalactone.

OR10Q1-variants were transiently expressed in HEK293 cells and then functionally characterized by Ca-imaging. A mutant of OR10Q1 was stimulated with pentadecalactone, but did not show any difference in comparison to the response of OR10Q1-WT.

Figure 13:
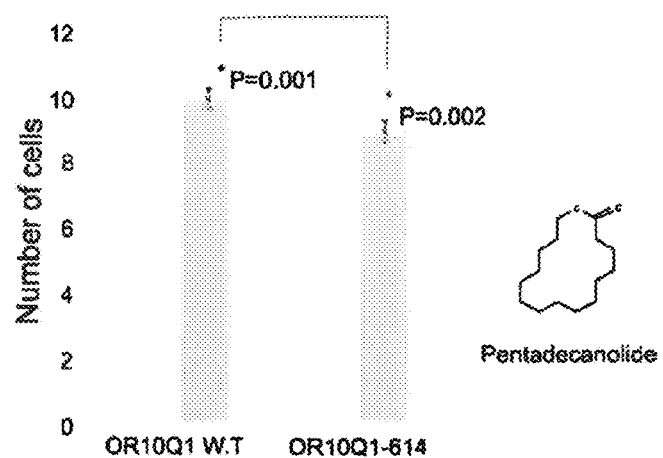
FIG. 13 illustrates a graph showing similar responses of OR10Q1-614 to pentadecanolide in comparison with OR10Q1 WT as examined by Ca-imaging measurements on mutated and WT receptor heterologous expressed in HEK293 cells.

FIG. 13 shows similar responses of OR10Q1-614 to pentadecanolide in comparison with OR10Q1 WT as examined by Ca-imaging measurements on mutated and WT receptor heterologous expressed in HEK293 cells. Odorant was applied for 20 seconds with concentration of 200 µM. Bars indicate the SEM (*p<0.05 according to Chi-square test). Control cells did not respond to pentadecanolide. There was no significant different response between OR10Q1 WT and OR10Q1-614. Approximately 2000 cells were screened during three times of measuring.

The invention claimed is:

1. A method for evaluating the scent performance of perfumes or perfume mixtures comprising odorants, said method comprising
   (a) bringing at least one odorant into contact with an olfactory receptor OR1B1 in vitro; and
   (b) measuring the response of the olfactory receptor OR1B1.

2. The method of claim 1, wherein said olfactory receptor OR1B1 is deorphanized.

3. The method of claim 1, wherein said odorants are subject to anosmia.

4. The method of claim 1, wherein said odorants comprise 6 to 9 carbon atoms.

5. The method of claim 1, wherein said odorants are selected from the group consisting of ketones, aldehydes, lactones, carboxylic acids and odorous steroids.

6. The method of claim 1, wherein the response of the olfactory receptor is measured by Ca-imaging.

7. The method of claim 1, wherein the response of the olfactory receptor is measured by CRE luciferase assay.

* * * * *

SEQUENCE LISTING

```
<160> NUMBER OF SEQ ID NOS: 15

<210> SEQ ID NO 1
<211> LENGTH: 10
<212> TYPE: PRT
<213> ORGANISM: Homo sapiens

<400> SEQUENCE: 1

Met Ala Tyr Asp Arg Tyr Val Ala Ile Cys
1               5                   10

<210> SEQ ID NO 2
<211> LENGTH: 77
<212> TYPE: DNA
<213> ORGANISM: Homo sapiens

<400> SEQUENCE: 2
gcatatgaat tcaccatggg tagcaacaag agcaagccca aggatgccag ccagcggatg     60
gagccccggg cggttgc                                                    77

<210> SEQ ID NO 3
<211> LENGTH: 37
<212> TYPE: DNA
<213> ORGANISM: Homo sapiens

<400> SEQUENCE: 3
```
gcatatgcgg ccgctcagtc agggtccgag tcagggt                                37

<210> SEQ ID NO 4
<211> LENGTH: 34
<212> TYPE: DNA
<213> ORGANISM: Homo sapiens

<400> SEQUENCE: 4
gcatatgaat tcatgatgag ctttgcccct aatg                                   34

<210> SEQ ID NO 5
<211> LENGTH: 35
<212> TYPE: DNA
<213> ORGANISM: Homo sapiens

<400> SEQUENCE: 5
gcatatgcgg ccgcggggtc taccttcacc cattc                                  35

<210> SEQ ID NO 6
<211> LENGTH: 32
<212> TYPE: DNA
<213> ORGANISM: Homo sapiens

<400> SEQUENCE: 6
gcatatgtcg acatgcctgt ggggaaactt gt                                     32

<210> SEQ ID NO 7
<211> LENGTH: 34
<212> TYPE: DNA
<213> ORGANISM: Homo sapiens

<400> SEQUENCE: 7
gcatatgcgg ccgctcagtt ggcgtcagag gctg                                   34

<210> SEQ ID NO 8
<211> LENGTH: 22
<212> TYPE: DNA
<213> ORGANISM: Homo sapiens

<400> SEQUENCE: 8
gaattggggc cactattcta cg                                                22

<210> SEQ ID NO 9
<211> LENGTH: 22
<212> TYPE: DNA
<213> ORGANISM: Homo sapiens

<400> SEQUENCE: 9
cgtagaatag tggccccaat tc                                                22

<210> SEQ ID NO 10
<211> LENGTH: 24
<212> TYPE: DNA
<213> ORGANISM: Homo sapiens

<400> SEQUENCE: 10
ccggccactt ctgtgagcct cttg                                              24

<210> SEQ ID NO 11
<211> LENGTH: 24
<212> TYPE: DNA
<213> ORGANISM: Homo sapiens -continued

```
<400> SEQUENCE: 11
caagaggctc acagaagtgg ccgg                                              24

<210> SEQ ID NO 12
<211> LENGTH: 22
<212> TYPE: DNA
<213> ORGANISM: Homo sapiens

<400> SEQUENCE: 12
cacctcattt gggtctactt cc                                                22

<210> SEQ ID NO 13
<211> LENGTH: 23
<212> TYPE: DNA
<213> ORGANISM: Homo sapiens

<400> SEQUENCE: 13
ggaagtagac ccaaatgatg gtg                                               23

<210> SEQ ID NO 14
<211> LENGTH: 22
<212> TYPE: DNA
<213> ORGANISM: Homo sapiens

<400> SEQUENCE: 14
ggaaatcaat cacttcctct gc                                                22

<210> SEQ ID NO 15
<211> LENGTH: 22
<212> TYPE: DNA
<213> ORGANISM: Homo sapiens

<400> SEQUENCE: 15
gcagaggaag tgattgattt cc                                                22
```